United States Patent
Baltezor et al.

(10) Patent No.: US 9,918,957 B2
(45) Date of Patent: Mar. 20, 2018

(54) METHODS FOR MAKING COMPOUND PARTICLES

(71) Applicant: CRITITECH, INC., Lawrence, KS (US)

(72) Inventors: Michael Baltezor, Lawrence, KS (US); Joseph Farthing, Lawrence, KS (US); Jake Sittenauer, Lawrence, KS (US); Jahna Espinosa, Lawrence, KS (US); Samuel Campbell, Lawrence, KS (US); Matthew McClorey, Lawrence, KS (US); Julia K. Fischer, Lawrence, KS (US); Mark D. Williams, Lawrence, KS (US)

(73) Assignee: Crititech, Inc., Lawrence, KS (US)

( * ) Notice: Subject to any disclaimer, the term of this patent is extended or adjusted under 35 U.S.C. 154(b) by 0 days.

(21) Appl. No.: 15/499,397

(22) Filed: Apr. 27, 2017

(65) Prior Publication Data
US 2017/0224650 A1    Aug. 10, 2017

Related U.S. Application Data

(60) Continuation of application No. 15/261,108, filed on Sep. 9, 2016, now abandoned, which is a division of application No. 15/174,505, filed on Jun. 6, 2016.
(Continued)

(51) Int. Cl.
*A61K 31/337*    (2006.01)
*A61K 9/16*    (2006.01)
(Continued)

(52) U.S. Cl.
CPC .......... *A61K 31/337* (2013.01); *A61K 9/1682* (2013.01); *B01J 3/008* (2013.01); *B01J 3/02* (2013.01)

(58) Field of Classification Search
None
See application file for complete search history.

(56) References Cited

U.S. PATENT DOCUMENTS

| 5,399,363 | A | 3/1995 | Liversidge et al. |
| 5,833,891 | A | 11/1998 | Subramaniam et al. |

(Continued)

FOREIGN PATENT DOCUMENTS

| WO | 2000/72827 | 12/2000 |
| WO | 2003/032906 | 4/2003 |

OTHER PUBLICATIONS

Kakran Mitali, et al., "Modified supercritical antisolvent method with enhanced mass transfer to fabricate drug nanoparticles," Materials Science and Engineering, 33(5): 2864-2870, Mar. 2013.
(Continued)

*Primary Examiner* — Aradhana Sasan
(74) *Attorney, Agent, or Firm* — McDonnell Boehnen Hulbert & Berghoff LLP

(57) ABSTRACT

Compositions are provided that include having at least 95% by weight of a taxane, or a pharmaceutically acceptable salt thereof, where the particles have a mean bulk density between about 0.050 g/cm³ and about 0.15 g/cm³, and/or a specific surface area (SSA) of at least 18 m²/g, 20 m²/g, 25 m²/g, 30 m²/g, 32 m²/g, 34 m²/g, or 35 m²/g. Methods for making and using such compositions are also provided.

18 Claims, 7 Drawing Sheets

Related U.S. Application Data

(60) Provisional application No. 62/171,060, filed on Jun. 4, 2015, provisional application No. 62/171,001, filed on Jun. 4, 2015, provisional application No. 62/171,008, filed on Jun. 4, 2015.

(51) Int. Cl.
*B01J 3/02* (2006.01)
*B01J 3/00* (2006.01)

(56) References Cited

U.S. PATENT DOCUMENTS

| | | |
|---|---|---|
| 5,874,029 A | 2/1999 | Subramaniam et al. |
| 6,113,795 A | 9/2000 | Subramaniam et al. |
| 6,562,952 B1 | 5/2003 | Rajewski et al. |
| 7,744,923 B2 | 6/2010 | Rajewski et al. |
| 8,221,779 B2 | 7/2012 | Jonas et al. |
| 8,778,181 B1 | 7/2014 | Johnson et al. |
| 9,233,348 B2 | 1/2016 | Johnson et al. |
| 2004/0033267 A1 | 2/2004 | Merisko-Liversidge et al. |
| 2006/0188566 A1 | 8/2006 | Liversidge et al. |
| 2008/0089944 A1 | 4/2008 | Rajewski et al. |
| 2012/0087984 A1 | 4/2012 | Liversidge et al. |
| 2012/0237768 A1 | 9/2012 | Hirokawa et al. |
| 2015/0342872 A1 | 12/2015 | Williamson et al. |
| 2015/0375153 A1 | 12/2015 | Johnson et al. |

OTHER PUBLICATIONS

Lee, et al., "Supercritical antisolvent production of biodegradable micro- and nanoparticles for controlled delivery of paclitaxel," Journal of Controlled Release, 125(2): 96-106, Oct. 2007.

International Search Report and Written Opinion for PCT/US2016/035993, dated Sep. 19, 2016.

Merisko-Liversidge, et al., "Formulation and Antitumor Activity Evaluation of Nanocrystalline Suspensions of Poorly Soluble Anticancer Drugs," Pharmaceutical Research, 13(2): 272-278, 1996.

Merisko-Liversidge, et al., "Nanosizing: a formulation approach for poorly-water-soluble compounds," European Journal of Pharmaceuticals Sciences, 18 (2003): 113-120.

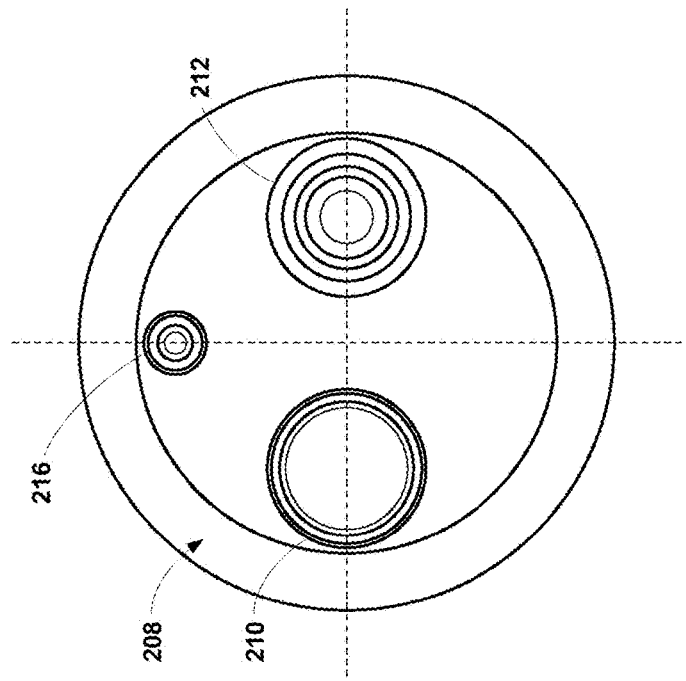
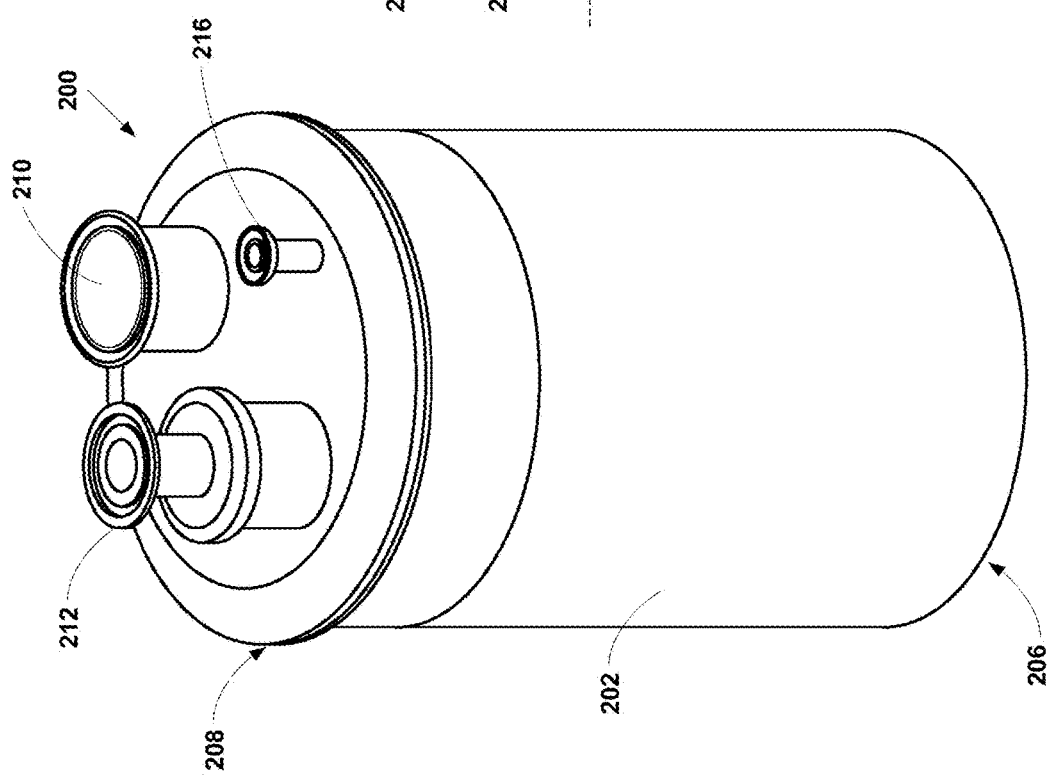

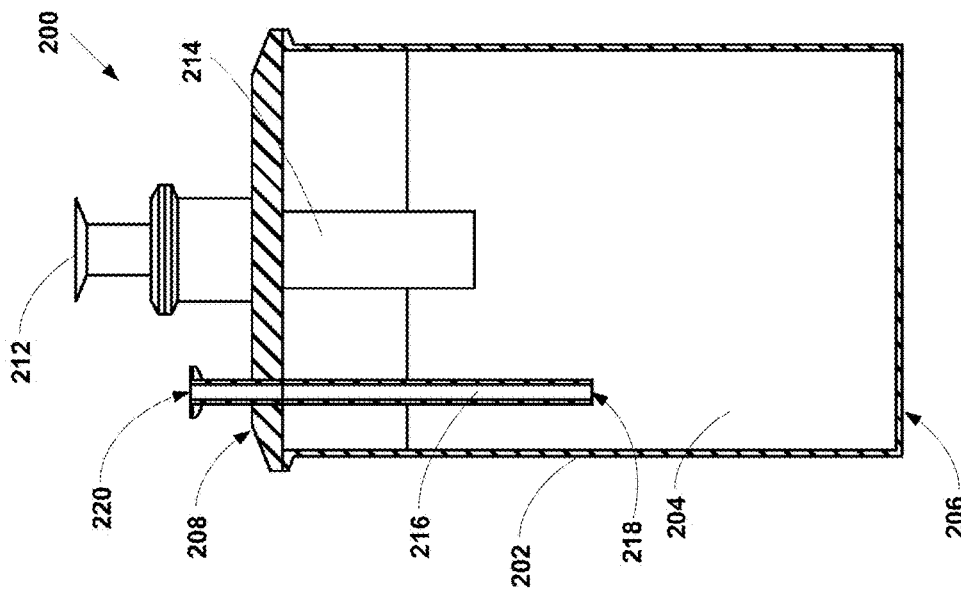
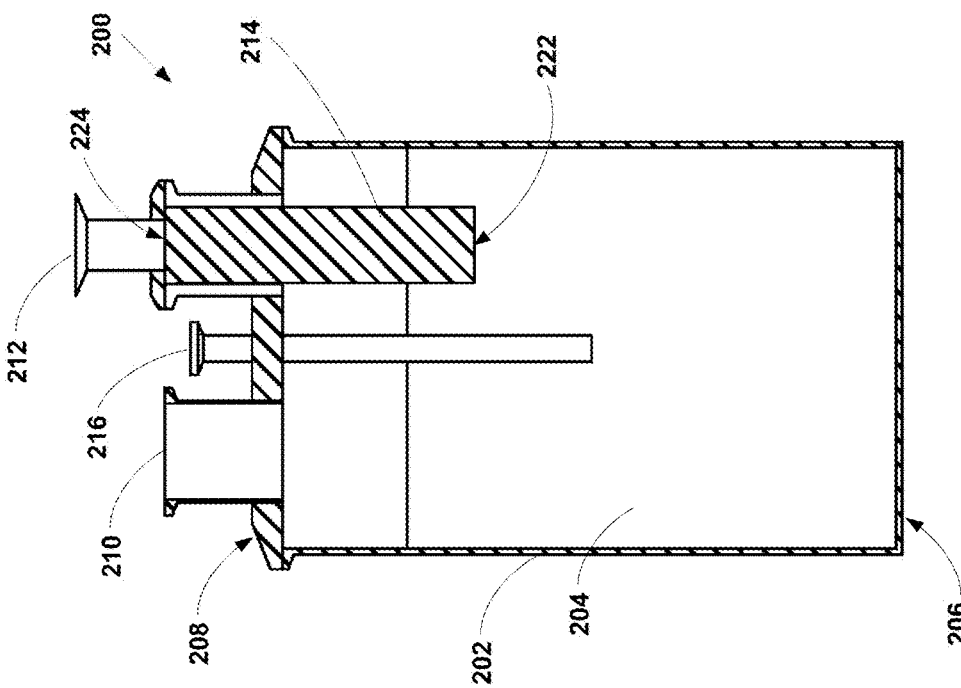

METHODS FOR MAKING COMPOUND PARTICLES

CROSS REFERENCE

This application is a continuation of U.S. application Ser. No. 15/261,108 filed Sep. 9, 2016, which is a divisional of U.S. patent application Ser. No. 15/174,505 filed Jun. 6, 2016, which claims priority to U.S. Provisional Patent Application Ser. Nos. 62/171,060 filed Jun. 4, 2015, 62/171,001 filed Jun. 4, 2015, and 62/171,008 filed Jun. 4, 2015, each incorporated by reference herein in its entirety.

BACKGROUND

Dissolution rate is a key parameter in determining the rate and extent of drug absorption and bioavailability. Poor aqueous solubility and poor in vivo dissolution are limiting factors for in vivo bioavailability of many drugs. Thus, in vitro dissolution rates are recognized as an important element in drug development, and methods and compositions for increasing the dissolution rates of poorly soluble drugs are needed.

SUMMARY OF THE INVENTION

In a first aspect, the invention provides compositions, comprising particles including at least 95% by weight of a taxane, or a pharmaceutically acceptable salt thereof, wherein the particles have one or both of the following characteristics:

(i) a mean bulk density between about 0.050 g/cm$^3$ and about 0.15 g/cm$^3$, and/or;

(ii) have a specific surface area (SSA) of at least 18 m$^2$/g, 20 m$^2$/g, 25 m$^2$/g, 30 m$^2$/g, 32 m$^2$/g, 34 m$^2$/g, or 35 m$^2$/g.

In one embodiment, the taxane is selected from the group consisting of paclitaxel, docetaxel, cabazitaxel, taxadiene, baccatin III, taxchinin A, brevifoliol, and taxuspine D, or a pharmaceutically acceptable salt thereof. In another embodiment, the taxane is selected from the group consisting of paclitaxel, docetaxel, and cabazitaxel, or a pharmaceutically acceptable salt thereof.

In a further embodiment, the taxane is paclitaxel or a pharmaceutically acceptable salt thereof, and wherein the particles have a mean bulk density between about 0.050 g/cm$^3$ and about 0.12 g/cm$^3$, or between about 0.060 g/cm$^3$ and about 0.11 g/cm$^3$. The paclitaxel particles may have a specific surface area (SSA) of at least 18 m$^2$/g, 20 m$^2$/g, 25 m$^2$/g, 30 m$^2$/g, 32 m$^2$/g, 34 m$^2$/g, or 35 m$^2$/g. The paclitaxel particles may have a SSA of between about 22 m$^2$/g and about 40 m$^2$/g, 25 m$^2$/g and about 40 m$^2$/g, 30 m$^2$/g and about 40 m$^2$/g, or between about 35 m$^2$/g and about 40 m$^2$/g. The paclitaxel particles may have a bulk density of between about 0.060 g/cm$^3$ and about 0.11 g/cm$^3$ and a SSA of between about 22 m$^2$/g and about 40 m$^2$/g. In another embodiment, at least 40% (w/w) of the paclitaxel is dissolved in 30 minutes or less in a solution of 50% methanol/50% water ((v/v)) at 37° C. and pH 7.0 in a USP II paddle apparatus operating at 75 RPM.

In one embodiment, the taxane is docetaxel or a pharmaceutically acceptable salt thereof, and wherein the particles have a mean bulk density between about 0.050 g/cm$^3$ and about 0.12 g/cm$^3$, or between about 0.06 g/cm$^3$ and about 0.1 g/cm$^3$. The docetaxel particles may have a SSA of at least 18 m$^2$/g, 20 m$^2$/g, 25 m$^2$/g, 30 m$^2$/g, 35 m$^2$/g, 40 m$^2$/g, or 42 m$^2$/g. The docetaxel particles may have a SSA of between about 40 m$^2$/g and about 50 m$^2$/g, or between about 43 m$^2$/g and about 46 m$^2$/g. The docetaxel particles may have a bulk density of between about 0.06 g/cm$^3$ and about 0.1 g/cm$^3$ and a SSA of between about 40 m$^2$/g and about 50 m$^2$/g. In a further embodiment, at least 20% (w/w) of the docetaxel is dissolved in 30 minutes or less in a solution of 15% methanol/85% water (v/v) at 37° C. and pH 7.0 in a USP II paddle apparatus operating at 75 RPM.

In a further aspect, the invention provides compositions comprising particles including at least 95% by weight of paclitaxel, or a pharmaceutically acceptable salt thereof, wherein the particles have a specific surface area (SSA) of at least 12 m$^2$/g. The paclitaxel particles may have a SSA of at least 12 m$^2$/g, 15 m$^2$/g, 20 m$^2$/g, 25 m$^2$/g, 30 m$^2$/g, 32 m$^2$/g, 34 m$^2$/g, or 35 m$^2$/g. In one embodiment, at least 40% (w/w) of the paclitaxel is dissolved in 30 minutes or less in a solution of 50% methanol/50% water (v/v) at 37° C. and pH 7.0 in a USP II paddle apparatus operating at 75 RPM.

In another aspect, the invention provides compositions comprising particles including at least 95% by weight of paclitaxel, wherein at least 40% (w/w) of the paclitaxel is dissolved in 30 minutes or less in a solution of 50% methanol/50% water (v/v) in a USP II paddle apparatus operating at 75 RPM. The invention also provides compositions comprising including at least 95% by weight of docetaxel, wherein at least 20% (w/w) of the docetaxel is dissolved in 30 minutes or less in a solution of 15% methanol/85% water (v/v) at 37° C. and pH 7.0 in a USP II paddle apparatus operating at 75 RPM.

The compositions of the invention may comprise particles have a mean particle size of between about 0.4 µm and about 1.2 µm, or between about 0.6 µm and about 1.0 µm. The particles may be uncoated and exclude polymer, protein, polyethoxylated castor oil and polyethylene glycol glycerides composed of mono-, di- and triglycerides and mono- and diesters of polyethylene glycol. The compositions may further be incorporated into a suspension, which further comprises a pharmaceutically acceptable aqueous carrier. The composition may further comprise one or more components selected from the group consisting of polysorbate, methylcellulose, polyvinylpyrrolidone, mannitol, and hydroxypropyl methylcellulose. The compositions may comprise by weight at least 96%, 97%, 98%, 99%, or 100% of the compound.

The invention further provides methods for treating a tumor, comprising administering to a subject with a tumor an amount effective to treat the tumor of a composition according to any embodiment or combination of embodiments of the invention. In one embodiment, the tumor may be selected from the group consisting of a breast tumor, an ovarian tumor, a lung tumor, a bladder tumor, a prostate tumor, a bone tumor, a stomach tumor and a pancreatic tumor. In another embodiment, the composition is administered intraperitoneally, such as by perfusion or as a bolus into the peritoneal cavity. In one embodiment, the intraperitoneal administration is initiated after removal of ascites fluid from the peritoneal cavity. In another embodiment, the subject is a human subject.

The invention further provides methods for making compound particles, comprising:

(a) introducing (i) a solution comprising at least one solvent and at least one solute comprising a compound of interest into a nozzle inlet, and (ii) a compressed fluid into an inlet of a vessel defining a pressurizable chamber;

(b) passing the solution out of a nozzle orifice and into the pressurizable chamber to produce an output stream of atomized droplets, wherein the nozzle orifice is located between 2 mm and 20 mm from a sonic energy source located within the output stream, wherein the sonic energy source produces sonic energy with an amplitude between 10% and 100% during the passing, and wherein the nozzle orifice has a diameter of between 20 μm and 125 μm; and (c) contacting the atomized droplets with the compressed fluid, to cause depletion of the solvent from the atomized droplets, to produce compound particles, wherein steps (a), (b), and (c) are carried out under supercritical temperature and pressure for the compressed fluid.

In one embodiment, the method further comprises:

(d) contacting the atomized droplets produced in step (c) with an anti-solvent to cause further depletion of the solvent from the compound particles, wherein step (d) is carried out under supercritical temperature and pressure for the anti-solvent.

In one embodiment, a flow rate of the solution through the nozzle has a range from about 0.5 mL/min to about 30 mL/min. In a further embodiment, the sonic energy source comprises one of a sonic horn, a sonic probe, or a sonic plate. In another embodiment, the sonic energy source has a frequency between about 18 kHx and about 22 kHz, or about 20 kHz.

The methods may further comprise:

(e) receiving the plurality of particles through the outlet of the pressurizable chamber; and (f) collecting the plurality of particles in a collection device.

In one embodiment, the compound is a taxane. The method of any one of claims 30-35 wherein the compound is a taxane. Exemplary taxanes may include paclitaxel, docetaxel, cabazitaxel, taxadiene, baccatin III, taxchinin A, brevifoliol, and taxuspine D, or a pharmaceutically acceptable salt thereof. In a specific embodiment, the taxane is selected from the group consisting of paclitaxel, docetaxel, and cabazitaxel, or a pharmaceutically acceptable salt thereof. In one embodiment, the solvent is selected from the group consisting of acetone, ethanol, methanol, dichloromethane, ethyl acetate, chloroform, acetonitrile, and suitable combinations thereof. In various embodiments, the compressed fluid and/or the anti-solvent may be super critical carbon dioxide. In one embodiment, the compound is paclitaxel and the solvent comprises acetone. In another embodiment, the compound is docetaxel and the solvent comprises ethanol. In a further embodiment, the method is carried out between 31.1° C. to about 60° C., and at between about 1071 psi and about 1800 psi.

The invention also provides compound particles prepared by the method of any embodiment or combination of embodiments of the invention.

BRIEF DESCRIPTION OF THE FIGURES

FIG. 5 illustrates a perspective view of a particle collection device, according to an example embodiment.

FIG. 6 illustrates a top view of the particle collection device, according to an example embodiment.

FIG. 7 illustrates a cross-section view of the particle collection device, according to an example embodiment.

FIG. 8 illustrates another cross-section view of the particle collection device, according to an example embodiment.

DETAILED DESCRIPTION OF THE INVENTION

Figure 1:
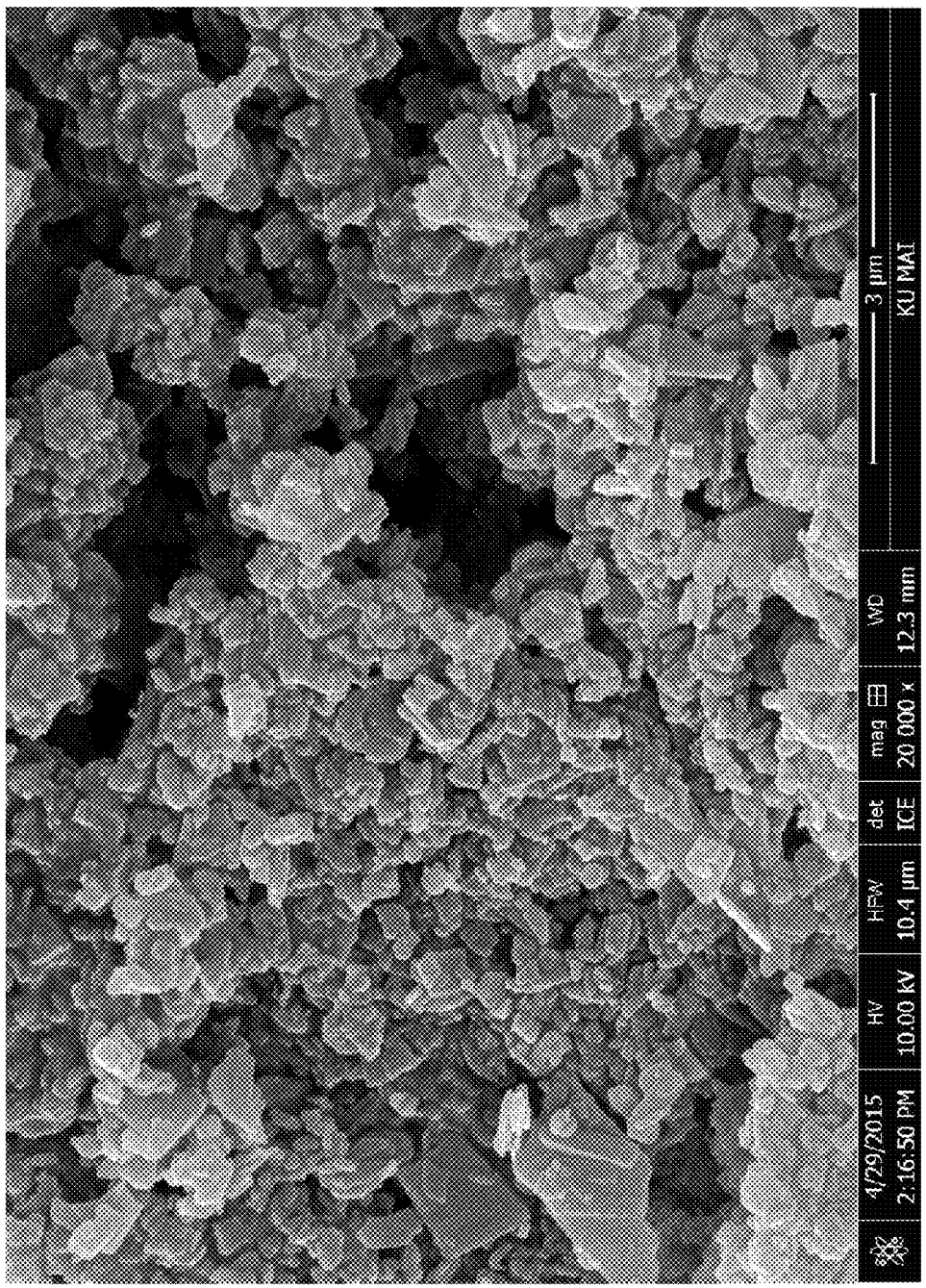
FIG. 1 is an electron micrograph of exemplary paclitaxel particles of the invention.
Figure 2:
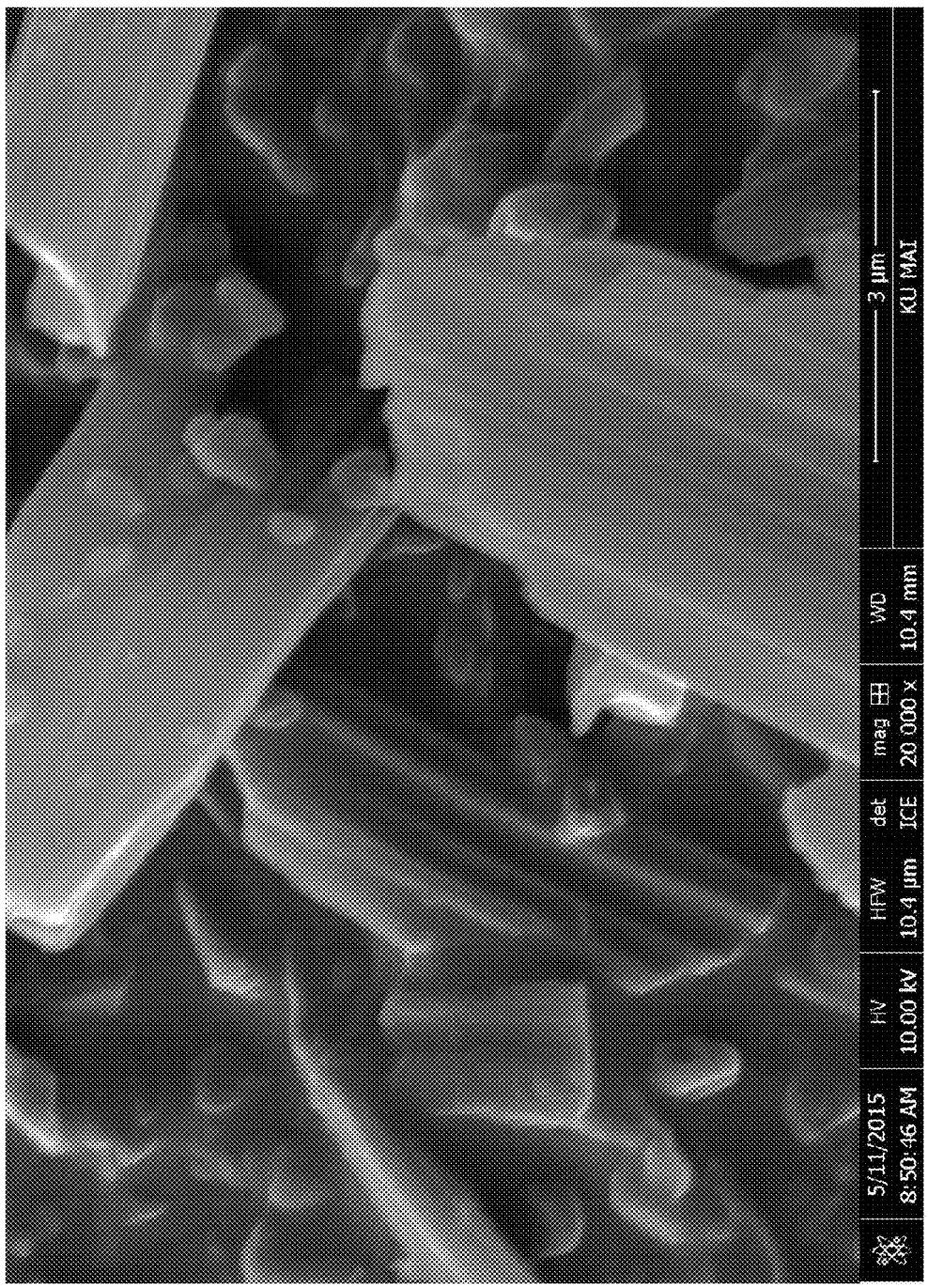
FIG. 2 is an electron micrograph of raw paclitaxel particles.

All references cited are herein incorporated by reference in their entirety. As used herein, the singular forms "a", "an" and "the" include plural referents unless the context clearly dictates otherwise. "And" as used herein is interchangeably used with "or" unless expressly stated otherwise. All embodiments of any aspect of the invention can be used in combination, unless the context clearly dictates otherwise.

As used herein, "about" means+/−5% of the recited value.

In one aspect, the present invention provides compositions, comprising particles including at least 95% by weight of a taxane, or a pharmaceutically acceptable salt thereof, wherein the particles have one or both of the following characteristics:

(i) a mean bulk density between about 0.050 g/cm$^3$ and about 0.15 g/cm$^3$, and/or (ii) have a specific surface area (SSA) of at least 18 m$^2$/g, 20 m$^2$/g, 25 m$^2$/g, 30 m$^2$/g, 32 m$^2$/g, 34 m$^2$/g, or 35 m$^2$/g.

The inventors have unexpectedly been able to produce compositions comprising the recited taxane particles that have a mean bulk density between about 0.050 g/cm$^3$ and about 0.15 g/cm$^3$, and/or a specific surface area (SSA) of at least 18 m$^2$/g an SSA using novel methods for producing the particles as described herein. As shown in the examples that follow, the increased specific surface area and decreased bulk density of the taxane particles result in significant increases in dissolution rate compared to the raw taxane and to milled taxane products used for comparison. Dissolution takes place only at a solid/liquid interface. Therefore, increased specific surface area will increase the dissolution rate due to a larger number of molecules on the surface of the particle having contact with the dissolution media. The bulk density takes into account the macrostructure and inter-particle space of a powder. Parameters that contribute to the bulk density include particle size distribution, particle shape, and the affinity of the particles for each other (i.e., agglomeration). Lower powder bulk densities yield faster dissolution rates. This is due to the ability of the dissolution media to more readily penetrate the interstitial or inter-particle spaces and have greater contact with the surface of the particles. Therefore, each of the increased specific surface area and the decreased bulk density result in the significant increase in dissolution rate for the taxane particles of the invention compared to the unprocessed or raw material, and the milled taxane product used for comparison. This provides a significant improvement for use of the taxane particles of the invention in, for example, tumor treatment.

As used herein, the "specific surface area" is the total surface area of the paclitaxel particle per unit of paclitaxel mass as measured by the Brunauer-Emmett-Teller ("BET") isotherm (i.e.: the BET SSA). As will be understood by those of skill in the art, the "taxane particles" include both agglomerated taxane particles and non-agglomerated taxane particles; since the SSA is determined on a per gram basis it takes into account both agglomerated and non-agglomerated taxane particles in the composition. The BET specific surface area test procedure is a compendial method included in both the United States Pharmaceopeia and the European Pharmaceopeia.

As used herein, the bulk density of the taxane particles is the mass of the totality of particles in the composition divided by the total volume they occupy when poured into a graduated cylinder. The total volume includes particle volume, inter-particle void volume, and internal pore volume.

Taxanes are a class of diterpenoids containing a taxadiene core that are very poorly soluble in water. The taxane particles of the invention may be any suitable taxane, including but not limited to paclitaxel, docetaxel, cabazitaxel, taxadiene, baccatin III, taxchinin A, brevifoliol, and taxuspine D, combinations thereof, or pharmaceutically acceptable salts thereof. In one embodiment, the taxane is selected from the group consisting of paclitaxel, docetaxel, and cabazitaxel, or a pharmaceutically acceptable salt thereof.

The "taxane particles" refers to particles of taxane that do not include an added excipient. Taxane particles are different than "particles containing taxane", which are particles that contain taxane and at least one added excipient. Taxane particles of the invention exclude a polymeric, wax or protein excipient and are not embedded, contained, enclosed or encapsulated within a solid excipient. Taxane particles of the invention may, however, contain impurities and byproducts typically found during preparation of taxane. Even so, taxane particles comprise at least 95%, at least 96%, at least 97%, at least 98%, at least 99% or 100% taxane, meaning the taxane particles consist of or consist essentially of substantially pure taxane. In one embodiment, the taxane particles are uncoated and exclude polymer, protein, polyethoxylated castor oil and polyethylene glycol glycerides composed of mono-, di- and triglycerides and mono- and diesters of polyethylene glycol.

The compositions of the invention have a mean particle size of between in the range of about 0.2 μm to about 5 μm, about 0.4 μm to about 3 μm or about 0.5 μm to about 1.4 μm. In a further embodiment, the compositions have a mean particle size of between about 0.4 μm and about 1.2 μm. In another embodiment the mean particle size is between about 0.4 μm and about 1.2 μm, or between about 0.6 μm and about 1.0 μm.

In one embodiment, the taxane is paclitaxel or a pharmaceutically acceptable salt thereof, and the particles have a mean bulk density between about 0.050 g/cm$^3$ and about 0.12 g/cm$^3$. In another embodiment, the paclitaxel particles have a mean bulk density between about 0.060 g/cm$^3$ and about 0.11 g/cm$^3$.

In a further embodiment, the taxane is paclitaxel or a pharmaceutically acceptable salt thereof, and wherein the paclitaxel particles have a specific surface area (SSA) of at least 18 m$^2$/g. In various further embodiments, the paclitaxel particles have a SSA of at least 20 m$^2$/g, 25 m$^2$/g, 30 m$^2$/g, 32 m$^2$/g, 34 m$^2$/g, or 35 m$^2$/g. In a further embodiment, the paclitaxel particles have a SSA of between about 22 m$^2$/g and about 40 m$^2$/g, between about 25 m$^2$/g and about 40 m$^2$/g, between about 30 m$^2$/g and about 40 m$^2$/g, or between about 35 m$^2$/g and about 40 m$^2$/g.

In one preferred embodiment, the paclitaxel particles have a mean bulk density of between about between about 0.050 g/cm$^3$ and about 0.12 g/cm$^3$ and a SSA of at least 30 m$^2$/g. In another preferred embodiment, the paclitaxel particles have a mean bulk density of between about between about 0.050 g/cm$^3$ and about 0.12 g/cm$^3$ and a SSA of at least 35 m$^2$/g. In one the paclitaxel particles have a mean bulk density of between about between about 0.050 g/cm$^3$ and about 0.12 g/cm$^3$ and a SSA of between about 30 m$^2$/g and about 40 m$^2$/g. In another preferred embodiment, the paclitaxel particles have a mean bulk density of between about 0.060 g/cm$^3$ and about 0.11 g/cm$^3$ and a SSA of between about 30 m$^2$/g and about 40 m$^2$/g. In another preferred embodiment, the paclitaxel particles have a mean bulk density of between about 0.060 g/cm$^3$ and about 0.11 g/cm$^3$ and a SSA of at least 30 m$^2$/g. In a further embodiment, the paclitaxel particles have a mean bulk density of between about 0.060 g/cm$^3$ and about 0.11 g/cm$^3$ and a SSA of at least 35 m$^2$/g. These various embodiments are exemplified in the examples that follow.

In any of these various embodiments, the paclitaxel particles may include at least $4.16 \times 10^{-13}$ gram paclitaxel, or a pharmaceutically acceptable salt thereof per paclitaxel particle.

In another embodiment, at least 40% (w/w) of the paclitaxel in the paclitaxel particles of the composition is dissolved in 30 minutes or less in a solution of 50% methanol/50% water (v/v) in a USP II paddle apparatus operating at 75 RPM. pH 7 was used, and the solubility of the taxanes are not effected by pH. In another embodiment, the dissolution studies are carried out at 37° C.

In another embodiment, the taxane is docetaxel or a pharmaceutically acceptable salt thereof, and the docetaxel particles have a mean bulk density between about 0.050 g/cm$^3$ and about 0.12 g/cm$^3$. In a further embodiment, the mean bulk density of the docetaxel particles is between about 0.06 g/cm$^3$ and about 0.1 g/cm$^3$.

In another embodiment, the taxane is docetaxel or a pharmaceutically acceptable salt thereof, and wherein the docetaxel particles have a SSA of at least 18 m$^2$/g. In various further embodiments, the docetaxel particles have a SSA of at least 20 m$^2$/g, 25 m$^2$/g, 30 m$^2$/g, 35 m$^2$/g, 40 m$^2$/g, or 42 m$^2$/g. In a further embodiment, the docetaxel particles have a SSA of between about 40 m$^2$/g and about 50 m$^2$/g. In another embodiment, the docetaxel particles have a SSA of between about 43 m$^2$/g and about 46 m$^2$/g.

In one preferred embodiment, the docetaxel particles have a mean bulk density between about 0.050 g/cm$^3$ and about 0.12 g/cm$^3$ and a SSA of at least 30 m$^2$/g. In another preferred embodiment, the docetaxel particles have a mean bulk density between about 0.050 g/cm$^3$ and about 0.12 g/cm$^3$ and a SSA of at least 35 m$^2$/g. In a further preferred embodiment, the docetaxel particles have a mean bulk density between about 0.050 g/cm$^3$ and about 0.12 g/cm$^3$ and a SSA of at least 40 m$^2$/g. In one preferred embodiment, the docetaxel particles have a mean bulk density between about 0.050 g/cm$^3$ and about 0.12 g/cm$^3$ and a SSA of between about 40 m$^2$/g and about 50 m$^2$/g. In another preferred embodiment, mean bulk density of the docetaxel particles is between about 0.06 g/cm$^3$ and about 0.1 g/cm$^3$ and the SSA is between about 40 m$^2$/g and about 50 m$^2$/g. These various embodiments are exemplified in the examples that follow.

In any of these various embodiments, the docetaxel particles may include at least $4.16 \times 10^{13}$ grams docetaxel, or a pharmaceutically acceptable salt thereof per docetaxel particle.

In another embodiment, at least 20% (w/w) of the docetaxel is dissolved in 30 minutes or less in a solution of 15% methanol/85% water (v/v) in a USP II paddle apparatus operating at 75 RPM. A neutral pH was used where the solubility of the taxanes are not effected by pH. In another embodiment, the dissolution studies are carried out at 37° C.

In a further aspect, the invention provides compositions comprising particles including at least 95% by weight of paclitaxel, or a pharmaceutically acceptable salt thereof, wherein the particles have a specific surface area (SSA) of at least 12 m²/g. In various embodiments, the paclitaxel particles have an SSA of at least 12, 13, 14, 15, 16, 17, 18, 19, 20, 21, 22, 23, 24, 25, 26, 27, 28, 29, 30, 31, 32, 33, 34, 35, 36, 37, 38, 39, or 40 m²/g. In various further embodiments, the paclitaxel particles have an SSA of between about 12 m²/g and about 40 m²/g, about 14 m²/g and about 40 m²/g, about 15 m²/g and about 40 m²/g, about 16 m²/g and about 40 m²/g, about 17 m²/g and about 40 m²/g, about 18 m²/g and about 40 m²/g, about 19 m²/g and about 40 m²/g, about 20 m²/g and about 40 m²/g, about 22 m²/g and about 40 m²/g, about 26 m²/g and about 40 m²/g, about 30 m²/g and about 40 m²/g, between about 20 m²/g and about 29 m²/g, between about 20 m²/g and about 28 m²/g, between about 20 m²/g and about 26.2 m²/g, between about 22 m²/g and about 29 m²/g, between about 22 m²/g and about 28 m²/g, between about 22 m²/g and about 26.2 m²/g, between about 32 m²/g and about 39 m²/g, between about 32 m²/g and about 38.5 m²/g, between about 32 m²/g and about 35 m²/g, between about 35 m²/g and about 40 m²/g, and between about 35 m²/g and about 38.5 m²/g. In other embodiments, the paclitaxel particles have an SSA of:

(a) between 16 m²/g and 31 m²/g or between 32 m²/g and 40 m²/g;
(b) between 16 m²/g and 30 m²/g or between 32 m²/g and 40 m²/g;
(c) between 16 m²/g and 29 m²/g or between 32 m²/g and 40 m²/g;
(d) between 17 m²/g and 31 m²/g or between 32 m²/g and 40 m²/g;
(e) between 17 m²/g and 30 m²/g or between 32 m²/g and 40 m²/g;
(f) between 17 m²/g and 29 m²/g, or between 32 m²/g and 40 m²/g;
(g) between 16 m²/g and 31 m²/g or between 33 m²/g and 40 m²/g;
(h) between 16 m²/g and 30 m²/g or between 33 m²/g and 40 m²/g;
(i) between 16 m²/g and 29 m²/g or between 33 m²/g and 40 m²/g;
(j) between 17 m²/g and 31 m²/g or between 33 m²/g and 40 m²/g;
(k) between 17 m²/g and 30 m²/g or between 33 m²/g and 40 m²/g;
(l) between 17 m²/g and 29 m²/g, or between 33 m²/g and 40 m²/g;
(m) between 16 m²/g and 31 m²/g, or ≥32 m²/g;
(h) between 17 m²/g and 31 m²/g, or ≥32 m²/g;
(i) between 16 m²/g and 30 m²/g, or ≥32 m²/g;
(j) between 17 m²/g and 30 m²/g, or ≥32 m²/g;
(k) between 16 m²/g and 29 m²/g, or ≥32 m²/g;
(l) between 17 m²/g and 29 m²/g, or ≥32 m²/g;
(m) between 16 m²/g and 31 m²/g, or ≥33 m²/g;
(n) between 17 m²/g and 31 m²/g, or ≥33 m²/g;
(o) between 16 m²/g and 30 m²/g, or ≥33 m²/g;
(p) between 17 m²/g and 30 m²/g, or ≥33 m²/g;
(q) between 16 m²/g and 29 m²/g, or ≥33 m²/g; or
(r) between 17 m²/g and 29 m²/g, or ≥33 m²/g.

In another embodiment, at least 40% (w/w) of the paclitaxel in the paclitaxel particles of the composition is dissolved in 30 minutes or less in a solution of 50% methanol/50% water (v/v) in a USP II paddle apparatus operating at 75 RPM. pH 7 was used, and the solubility of the taxanes are not effected by pH. In another embodiment, the dissolution studies are carried out at 37° C.

In another aspect, the present invention provides compositions, comprising particles including at least 95% by weight of paclitaxel, wherein at least 40% (w/w) of the paclitaxel is dissolved in 30 minutes or less in a solution of 50% methanol/50% water (v/v) in a USP II paddle apparatus operating at 75 RPM. pH 7 was used, and the solubility of the taxanes are not effected by pH. In another embodiment, the dissolution studies are carried out at 37° C.

In a further aspect, the present invention provides composition, comprising including at least 95% by weight of docetaxel, wherein at least 20% (w/w) of the docetaxel is dissolved in 30 minutes or less in a solution of 15% methanol/85% water (v/v) in a USP II paddle apparatus operating at 75 RPM. pH 7 was used, and the solubility of the taxanes are not effected by pH. In another embodiment, the dissolution studies are carried out at 37° C.

In a further embodiment, the composition comprises a suspension further comprising a pharmaceutically acceptable aqueous carrier. The suspension of the invention comprises taxane particles and a liquid carrier. The liquid carrier can be aqueous. The suspension excludes a solid excipient within which the paclitaxel is contained and excludes GELUCIRE® (polyethylene glycol glycerides composed of mono-, di- and triglycerides and mono- and diesters of polyethylene glycol), and CREMOPHOR® (polyethoxylated castor oil).

Even though the paclitaxel particles do not include an added excipient, the liquid carrier of the suspension can comprise water and optionally one or more excipients selected from the group consisting of buffer, tonicity adjusting agent, preservative, demulcent, viscosity modifier, osmotic agent, surfactant, antioxidant, alkalinizing agent, acidifying agent, antifoaming agent, and colorant. For example, the suspension can comprise taxane particles, water, buffer and salt. It optionally further comprises a surfactant. In some embodiments, the suspension consists essentially of or consists of water, taxane particles suspended in the water and buffer. The suspension can further contain an osmotic salt.

The suspension can comprise one or more surfactants. Suitable surfactants include by way of example and without limitation polysorbates, lauryl sulfates, acetylated monoglycerides, diacetylated monoglycerides, and poloxamers.

The suspension can comprise one or more tonicity adjusting agents. Suitable tonicity adjusting agents include by way of example and without limitation, one or more inorganic salts, electrolytes, sodium chloride, potassium chloride, sodium phosphate, potassium phosphate, sodium, potassium sulfates, sodium and potassium bicarbonates and alkaline earth metal salts, such as alkaline earth metal inorganic salts, e.g., calcium salts, and magnesium salts, mannitol, dextrose, glycerin, propylene glycol, and mixtures thereof.

In one embodiment especially suitable for intraperitoneal (IP) administration, the suspension may be formulated to be hyperosmolar (hypertonic), hyposmolar (hypotonic) or isosmolar (isotonic) with respect to the fluid(s) of the IP cavity. In some embodiments, the suspension may be isotonic with respect to fluid in the IP cavity. In such an embodiment, the he osmolality of the suspension can range from about 200 to about 380, about 240 to about 340, about 280 to about 300 or about 290 mOsm/kg.

The suspension can comprise one or more buffering agents. Suitable buffering agents include by way of example and without limitation, dibasic sodium phosphate, monobasic sodium phosphate, citric acid, sodium citrate hydrochloric acid, sodium hydroxide, tris(hydroxymethyl)aminomethane, bis(2-hydroxyethyl)iminotris-(hydroxymethyl)methane, and sodium hydrogen carbonate and others known to those of ordinary skill in the art. Buffers are commonly used to adjust the pH to a desirable range for intraperitoneal use. Usually a pH of around 5 to 9, 5 to 8, 6 to 7.4, 6.5 to 7.5, or 6.9 to 7.4 is desired.

The suspension can comprise one or more demulcents. A demulcent is an agent that forms a soothing film over a mucous membrane, such as the membranes lining the peritoneum and organs therein. A demulcent may relieve minor pain and inflammation and is sometimes referred to as a mucoprotective agent. Suitable demulcents include cellulose derivatives ranging from about 0.2 to about 2.5% such as carboxymethylcellulose sodium, hydroxyethyl cellulose, hydroxypropyl methylcellulose, and methylcellulose; gelatin at about 0.01%; polyols in about 0.05 to about 1%, also including about 0.05 to about 1%, such as glycerin, polyethylene glycol 300, polyethylene glycol 400, polysorbate 80, and propylene glycol; polyvinyl alcohol from about 0.1 to about 4%; povidone from about 0.1 to about 2%; and dextran 70 from about 0.1% when used with another polymeric demulcent described herein.

The suspension can comprise one or more alkalinizing agents to adjust the pH. As used herein, the term "alkalizing agent" is intended to mean a compound used to provide an alkaline medium. Such compounds include, by way of example and without limitation, ammonia solution, ammonium carbonate, potassium hydroxide, sodium carbonate, sodium bicarbonate, and sodium hydroxide and others known to those of ordinary skill in the art The suspension can comprise one or more acidifying agents to adjust the pH. As used herein, the term "acidifying agent" is intended to mean a compound used to provide an acidic medium. Such compounds include, by way of example and without limitation, acetic acid, amino acid, citric acid, nitric acid, fumaric acid and other alpha hydroxy acids, hydrochloric acid, ascorbic acid, and nitric acid and others known to those of ordinary skill in the art.

The suspension can comprise one or more antifoaming agents. As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE®, octoxynol and others known to those of ordinary skill in the art.

The suspension can comprise one or more viscosity modifiers that increase or decrease the viscosity of the suspension. Suitable viscosity modifiers include methylcellulose, hydroxypropyl methycellulose, mannitol and polyvinylpyrrolidone.

The suspension can comprise one or more osmotic agents such as those used for peritoneal dialysis. Suitable osmotic agents include icodextrin (a glucose polymer), sodium chloride, potassium chloride, and salts that are also used as buffering agents.

As used herein, "pharmaceutically acceptable salts" of the taxanes are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the taxanes. The term "salts" refers to the relatively non-toxic, inorganic and organic acid addition salts of taxanes. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," J. Pharm. Sci., 1977; 66:1-19 which is incorporated herein by reference.)

In one embodiment, the composition comprises a dosage form of taxane in suspension (i.e.: with a pharmaceutically acceptable carrier and any other components), in a dosage deemed suitable by an attending physician for an intended use. Any suitable dosage form may be used; in various non-limiting embodiments, the dosage form is adequate to provide about 0.01 mg/kg to about 50 mg/kg of body weight per day. In various further embodiments, the dosage form is adequate to provide about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg of body weight per day. The suspension can be administered as is or can be diluted with a diluent, e.g. with saline water for injection optionally including a buffering agent and one or more other excipients, prior to administration. For example, the volume ratio of suspension to diluent might be in the range of 1:1-1:100 (v/v) or other suitable ratio.

In another aspect, the invention provides methods for treating a tumor, comprising administering to a subject with a tumor an amount effective to treat the tumor of the composition or suspension of any embodiment or combination of embodiments of the invention. The inventors have unexpectedly been able to produce compositions comprising the recited taxane particles that have a mean bulk density between about 0.050 g/cm$^3$ and about 0.15 g/cm$^3$, and/or a specific surface area (SSA) of at least 18 m$^2$/g an SSA using novel methods for producing the particles as described herein. Each of the increased specific surface area and the decreased bulk density result in the significant increase in dissolution rate for the taxane particles of the invention compared to the unprocessed or raw material, and the milled taxane product used for comparison. This provides a significant improvement for use of the taxane particles of the invention in, for example, tumor treatment.

As used herein, a "tumor" includes benign tumors, pre-malignant tumors, malignant tumors that have not metastasized, and malignant tumors that have metastasized.

The methods of the invention can be used to treat tumor that is susceptible to taxane treatment, including but not limited to breast tumors, ovarian tumors, lung tumors, bladder tumors, prostate tumors, bone tumors, stomach tumors and pancreatic tumors. In one non-limiting embodiment, the tumor is located in whole or in part in the intraperitoneal cavity.

The subject may be any suitable subject with a tumor, including but not limited to humans, primates, dogs, cats, horses, cattle, etc.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

Amounts effective for these uses depend on factors including, but not limited to, the nature of the taxane (specific activity, etc.), the route of administration, the stage and severity of the disorder, the weight and general state of health of the subject, and the judgment of the prescribing physician. It will be understood that the amount of the composition of suspension of the invention actually administered will be determined by a physician, in the light of the above relevant circumstances. In one non-limiting embodiment, an amount effective is an amount that provides between 0.01 mg/kg to about 50 mg/kg of body weight per day.

The compositions may be administered via any suitable route, including but not limited to orally, pulmonary, intraperitoneally, subcutaneous injection, intramuscular injection, or any other form of injection, as deemed most appropriate by attending medical personnel in light of all factors for a given subject. In one embodiment, the composition or suspension is administered intraperitoneally, for example, when the tumor is located (at least in part) in the peritoneal cavity. In this embodiment, the composition or suspension may be administered, for example, by perfusion or as a bolus into the peritoneal cavity. In a further embodiment, the administering may be initiated after removal of ascites fluid from the peritoneal cavity.

A dosing period is that period of time during which a dose of taxane particles in the composition or suspension is administered. The dosing period can be a single period of time during which the entire dose is administered, or it can be divided into two or more periods of time during each of which a portion of the dose is administered.

A post-dosing period is that period of time beginning after completion of a prior dosing period and ending after initiating a subsequent dosing period. The duration of the post-dosing period may vary according to a subject's clinical response to the paclitaxel. The suspension is not administered during the post-dosing period. A post-dosing period can last at least 7 days, at least 14 days, at least 21 days, at least 28 days, at least 35 days, at least 60 days or at least 90 days or longer. The post-dosing period can be kept constant for a subject or two or more different post-dosing periods can be used for a subject.

A dosing cycle includes a dosing period and a post-dosing period. Accordingly, the duration of a dosing cycle will be the sum of the dosing period and the post-dosing period. The dosing cycle can be kept constant for a subject or two or more different dosing cycles can be used for a subject.

In one embodiment, the administering is carried out more than once, and wherein each administration is separated in time by at least 21 days.

In another aspect, the invention provides methods for making compound particles, comprising:

(a) introducing (i) a solution comprising at least one solvent and at least one solute comprising a compound of interest into a nozzle inlet, and (ii) a compressed fluid into an inlet of a vessel defining a pressurizable chamber;

(b) passing the solution out of a nozzle orifice and into the pressurizable chamber to produce an output stream of atomized droplets, wherein the nozzle orifice is located between 2 mm and 20 mm from a sonic energy source located within the output stream, wherein the sonic energy source produces sonic energy with an amplitude between 10% and 100% of the total power that can be generated using the sonic energy source during the passing, and wherein the nozzle orifice has a diameter of between 20 µm and 125 µm;

(c) contacting the atomized droplets with the compressed fluid, to cause depletion of the solvent from the atomized droplets, to produce compound particles;

wherein steps (a), (b), and (c) are carried out under supercritical temperature and pressure for the compressed fluid.

The methods of the invention involve contacting a solution, including a solvent with at least one compound of interest (including but not limited to an active pharmaceutical ingredient, such as a taxane) dispersed in the solvent, with a compressed fluid at supercritical conditions for the compressed fluid, so as to cause the compressed fluid to deplete the solvent and precipitate the compound away as extremely small particles.

The methods of the present invention provide a significant improvement over methods such as those disclosed in U.S. Pat. Nos. 5,833,891; 5,874,029; 6,113,795; and U.S. Pat. No. 8,778,181 (incorporated herein by reference in their entirety) using a compressed fluid in combination with appropriate solvents to reproducibly precipitate compounds as fine particles that have a narrow size distribution. The methods of the present invention are capable of producing the particles of the invention with significantly improved bulk density, SSA, and dissolution properties, and thus significantly improved therapeutic benefits. The methods provide this significant improvement, at least in part, through use of the sonic energy source external to the nozzle and at the recited distance from the nozzle orifice to provide significantly enhanced sonic energy and enhanced disruption of the solvent-solute flow as it exits the nozzle compared to the methods disclosed U.S. Pat. Nos. 5,833,891 and 5,874,029 that use a converging-diverging nozzle to create the sonic energy.

In one embodiment, the methods further comprise:

(d) contacting the atomized droplets produced in step (c) with an anti-solvent to cause further depletion of the solvent from the compound particles, wherein step (d) is carried out under supercritical temperature and pressure for the anti-solvent.

The methods of the invention utilize a sonic energy source located directly in the output stream of the solute dissolved in the solvent. Any suitable source of sonic energy may be used that is compatible with the methods of the invention, including but not limited to sonic horn, a sonic probe, or a sonic plate. In various embodiments, the nozzle orifice is located between about 2 mm and about 20 mm, about 2 mm and about 18 mm, about 2 mm and about 16 mm, about 2 mm and about 14 mm, about 2 mm and about 12 mm, about 2 mm and about 10 mm, about 2 mm and about 8 mm, about 2 mm and about 6 mm, about 2 mm and about 4 mm, about 4 mm and about 20 mm, about 4 mm and about 18 mm, about 4 mm and about 16 mm, about 4 mm and about 14 mm, about 4 mm and about 12 mm, about 4 mm and about 10 mm, about 4 mm and about 8 mm, about 4 mm and about 6 mm, about 6 mm and about 20 mm, about 6 mm and about 18 mm, about 6 mm and about 16 mm, about 6 mm and about 14 mm, about 6 mm and about 12 mm, about 6 mm and about 10 mm, about 6 mm and about 8 mm, about 8 mm and about 20 mm, about 8 mm and about 18 mm, about 8 mm and about 16 mm, about 8 mm and about 14 mm, about 8 mm and about 12 mm, about 8 mm and about 10 mm, about 10 mm and about 20 mm, about 10 mm and about 18 mm, about 10 mm and about 16 mm, about 10 mm and about 14 mm, about 10 mm and about 12 mm, about 12 mm and about 20 mm, about 12 mm and about 18 mm, about 12 mm and about 16 mm, about 12 mm and about 14 mm, about 14 mm and about 20 mm, about 14 mm and about 18 mm, about 14 mm and about 16 mm, about 16 mm and about 20 mm, about 16 mm and about 18 mm, and about 18 mm and about 20 mm, from the sonic energy source.

Figure 3:
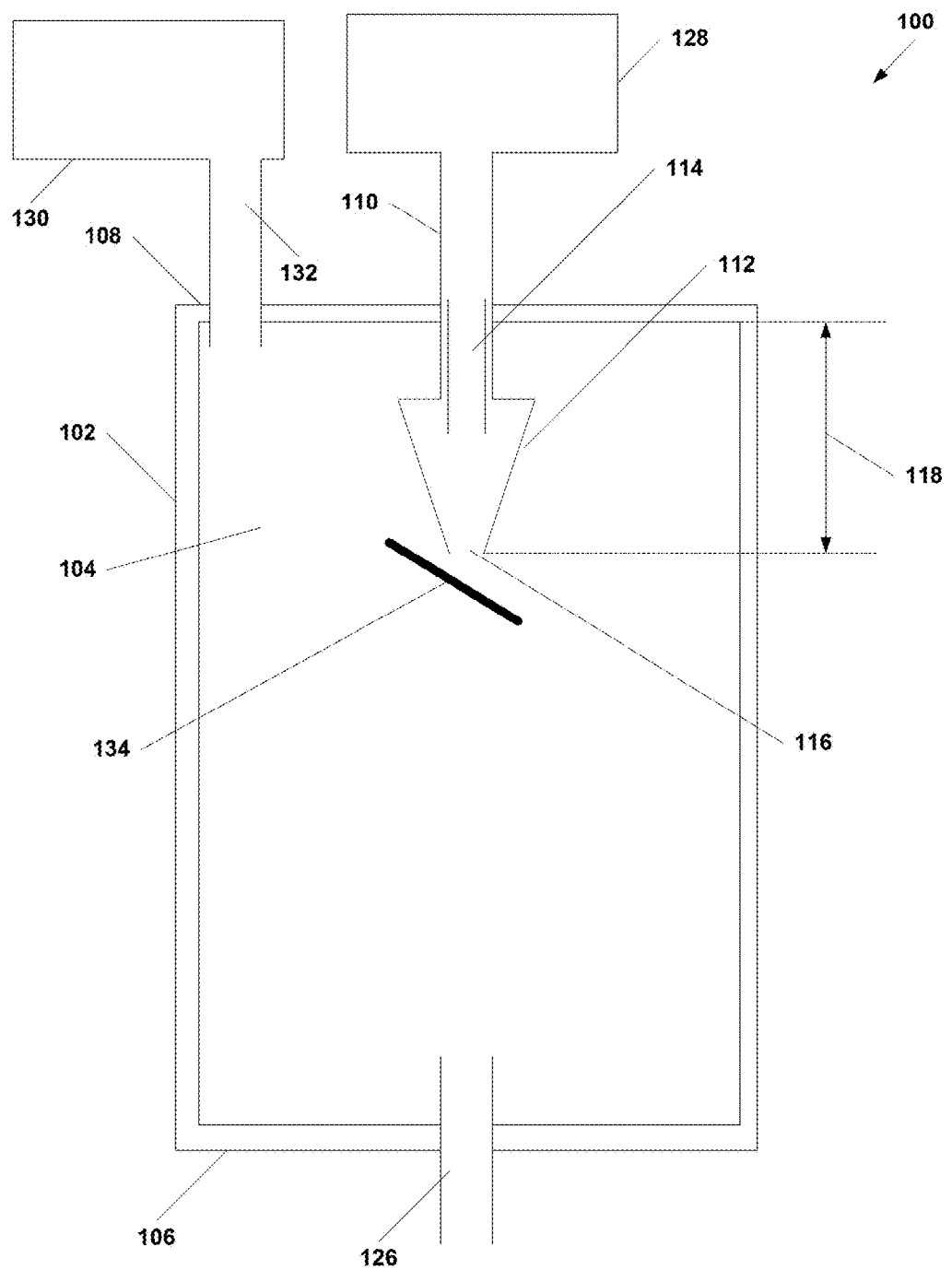
FIG. 3 illustrates a cross-section view of an example nozzle assembly, according to an example embodiment.

In further embodiments, with reference to the Figures, as shown in FIG. 3, the nozzle assembly 100 includes a vessel 102 defining a pressurizable chamber 104. The vessel 102 includes a distal end 106 and a proximal end 108. The nozzle assembly 100 further includes an inlet 110 of the pressurizable chamber 104 at the proximal end 108 of the vessel 102. The nozzle assembly 100 further includes a nozzle 112 positioned within the pressurizable chamber 104. As shown in FIG. 3, the nozzle 112 includes an inlet tube 114 in fluid communication with the inlet 110 of the pressurizable chamber 104. In addition, the nozzle 112 includes an outlet aperture 116. Further, as shown in FIG. 3, the nozzle 112 is adjustable to alter a distance 118 between the proximal end 108 of the vessel 102 and the outlet aperture 116 of the nozzle 112. As shown in FIG. 3, the nozzle 112 is further adjustable to alter an angle 120 between a longitudinal axis of the vessel 122 and a longitudinal axis of the nozzle 124. In addition, the nozzle assembly 100 includes an outlet 126 of the pressurizable chamber 104 at the distal end 106 of the vessel 102.

The nozzle assembly 100 may further include a first reservoir 128 and a second reservoir 130. The first reservoir 128 may include a supply of solvent, while the second reservoir 130 may include a supply of anti-solvent. The inlet 110 of the pressurizable chamber 104 may be in fluid communication with the first reservoir 128, and a second inlet 132 of the pressurizable chamber 104 may be in fluid communication with the second reservoir 130. In one example, the first reservoir 128 is in fluid communication with the inlet tube 114 of the nozzle 112, such that the solvent enters the pressurizable chamber 104 through the nozzle 112. Other examples are possible as well.

The outlet aperture 116 of the nozzle 112 may include a plurality of ridges to create a vortex within the nozzle 112 such that the solvent exits the nozzle 112 via turbulent flow. In another example, the nozzle 112 may include a porous frit interior to the nozzle 112 such that the solvent exits the nozzle 112 via turbulent flow. In yet another example, the outlet aperture 116 of the nozzle 112 may have a small diameter (as discussed in additional detail below) such that the solvent exits the nozzle 112 via turbulent flow. These various embodiments that cause turbulent flow may assist in mixing the solvent with the anti-solvent within the pressurizable chamber 104. Further, the inlet tube 114 of the nozzle 112 may have an inner diameter with a range from about 1.5875 mm to about 6.35 mm.

In one example, both the angle of the nozzle 112 and the vertical position of the nozzle 112 may be adjusted manually by a user. For example, the nozzle 112 may be positioned on a vertical support that can be adjusted to alter the distance 118 between the proximal end 108 of the vessel 102 and the outlet aperture 116 of the nozzle 112. Further, the nozzle 112 may be rotated manually to adjust the angle 120 between the longitudinal axis of the vessel 122 and the longitudinal axis of the nozzle 124.

In another example, the nozzle assembly 100 may include a motor coupled to the nozzle 112. In various examples, the motor may be configured to alter the distance 118 between the proximal end 108 of the vessel 102 and the outlet aperture 116 of the nozzle 112 and/or alter the angle 120 between the longitudinal axis of the vessel 122 and the longitudinal axis of the nozzle 124. Such a motor may be an electric motor powered by electrical power, or may be powered by a number of different energy sources, such as a gas-based fuel or solar power. The motor may be coupled directly or indirectly to the nozzle 112, such that when the motor is turned on the distance 118 between the proximal end 108 of the vessel 102 and the outlet aperture 116 of the nozzle 112 increases or decreases depending on the direction the motor rotates. The motor may be coupled to a series of gears that adjusts the distance 118 between the proximal end 108 of the vessel 102 and the outlet aperture 116 of the nozzle 112 and/or adjusts the angle 120 between the longitudinal axis of the vessel 122 and the longitudinal axis of the nozzle 124, or the motor may be coupled to a pulley system that adjusts the distance 118 between the proximal end 108 of the vessel 102 and the outlet aperture 116 of the nozzle 112 and/or adjusts the angle 120 between the longitudinal axis of the vessel 122 and the longitudinal axis of the nozzle 124. Other configurations are possible as well.

In another example, the nozzle 112 assembly may include an actuator coupled to the nozzle 112, where the actuator alters the distance 118 between the proximal end 108 of the vessel 120 and the outlet aperture 116 of the nozzle 112 and/or alters the angle 120 between the longitudinal axis of the vessel 122 and the longitudinal axis of the nozzle 124. Such an actuator may be an electro-mechanical actuator, including an electric motor that converts a rotary motion of the electric motor to a linear displacement via a linkage system. Other potential actuators are possible as well, such as hydraulic actuators, pneumatic actuators, piezoelectric actuators, linear motors, or telescoping linear actuators, as examples.

Figure 4:
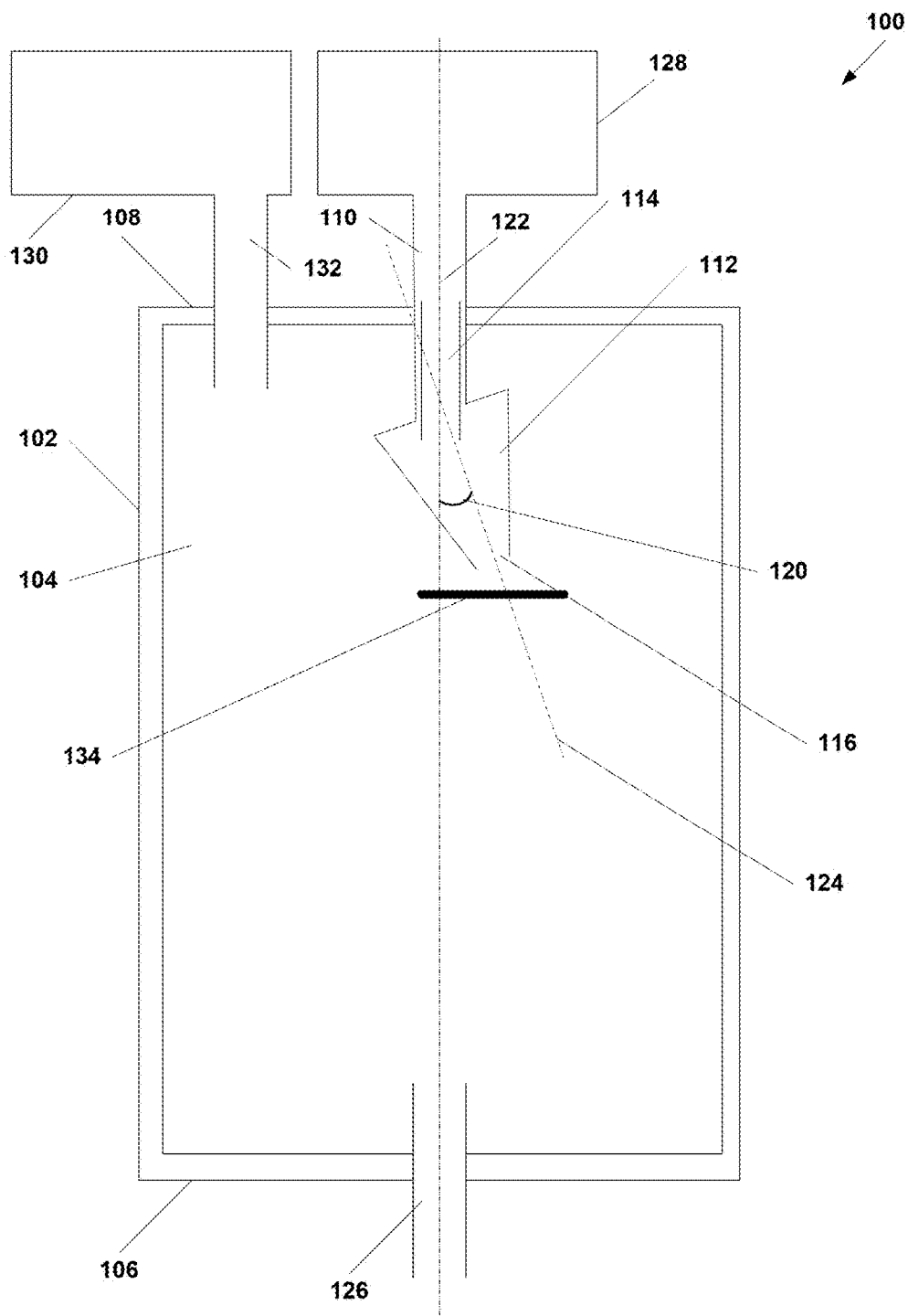
FIG. 4 illustrates a cross-section view of another example nozzle assembly, according to an example embodiment.

In one example, as shown in FIGS. 3 and 4, the nozzle assembly further includes a sonic energy source 134 positioned adjacent to the outlet aperture 116 of the nozzle 112. In one example, the sonic energy source 134 may include a sonic probe extending within the pressurizable chamber 104. In another example, the sonic energy source 134 may include a sonic surface positioned in the pressurizable chamber 104. The sonic waves from the sonic energy source 134 cause the liquids in the pressurizable chamber 104 to shatter, thereby enhancing mixing of the solvent and anti-solvent solutions to create particles within the pressurizable chamber 104. In one example, the sonic energy source 134 is positioned at an angle of 45 degrees with respect to the longitudinal axis of the nozzle 124. Other angles are possible as well. In one example, the sonic energy source 134 may be adjustable to alter a distance between the outlet aperture 116 of the nozzle 112 and the sonic energy source 134. Further, the sonic energy source 134 may be adjustable to alter an angle between the sonic energy source 134 and the longitudinal axis of the nozzle 124.

Any suitable source of sonic energy may be used that is compatible with the methods of the invention, including but not limited to sonic horn, a sonic probe, or a sonic plate. In various further embodiments, the sonic energy source produces sonic energy with an amplitude between about 1% and about 100% of the total power that can be generated using the sonic energy source. In light of the teachings herein, one of skill in the art can determine an appropriate sonic energy source having a specific total power output to be used. In one embodiment, the sonic energy source has a total power output of between about 500 and about 900 watts; in various further embodiments, between about 600 and about 800 watts, about 650-750 watts, or about 700 watts.

In various further embodiments, the sonic energy source produces sonic energy with a power output between about 5% and about 100%, about 10% and about 100%, 20% and about 100%, about 30% and about 100%, about 40% and about 100%, about 50% and about 100%, about 60% and about 100%, about 70% and about 100%, about 80% and about 100%, about 90% and about 100%, about 1% and about 90%, about 5% and about 90%, about 10% and about 90%, about 20% and about 90%, about 30% and about 90%, about 40% and about 90%, about 50% and about 90%, about 60% and about 90%, about 70% and about 90%, about 80% and about 90%, about 1% and about 80%, about 5% and about 80%, about 10% and about 80%, about 20% and about 80%, about 30% and about 80%, about 40% and about 80%, about 50% and about 80%, about 60% and about 80%, about 70% and about 80%, about 1% and about 70%, about 5% and about 70%, about 10% and about 70%, about 20% and about 70%, about 30% and about 70%, about 40% and about 70%, about 50% and about 70%, about 60% and about 70%, about 1% and about 60%, about 5% and about 60%, about 10% and about 60%, about 20% and about 60%, about 30% and about 60%, about 40% and about 60%, about 50% and about 60%, about 1% and about 50%, about 5% and about 50%, about 10% and about 50%, about 20% and about 50%, about 30% and about 50%, about 40% and about 50%, about 1% and about 40%, about 5% and about 40%, about 10% and about 40%, about 20% and about 40%, about 30% and about 40%, about 1% and about 30%, about 5% and about 30%, about 10% and about 30%, about 20% and about 30%, about 1% and about 20%, about 5% and about 20%, about 10% and about 20%, about 1%, 5%, 10%, 20%, 30%, 40%, 50%, 60%, 70%, 80%, 90%, or about 100% of the total power that can be generated using the sonic energy source. In various embodiments, the sonic energy source produces sonic energy with power output of about 1%-80%, 20-80%, 30-70%, 40-60%, or about 60% of the total power that can be generated using the sonic energy source. In light of the teachings herein, one of skill in the art can determine an appropriate frequency to be utilized on the sonic energy source. In one embodiment, a frequency of between about 18 and about 22 kHz on the sonic energy source is utilized. In various other embodiments, a frequency of between about 19 and about 21 kHz, about 19.5 and about 20.5, or, a frequency of about 20 kHz on the sonic energy source is utilized.

In various further embodiments, the nozzle orifice has a diameter of between about 20 µm and about 125 about 20 µm and about 115 about 20 µm and about 100 about 20 µm and about 90 about 20 µm and about 80 about 20 µm and about 70 about 20 µm and about 60 about 20 µm and about 50 about 20 µm and about 40 about 20 µm and about 30 between about 30 µm and about 125 about 30 µm and about 115 about 30 µm and about 100 about 30 µm and about 90 about 30 µm and about 80 about 30 µm and about 70 about 30 µm and about 60 about 30 µm and about 50 about 30 µm and about 40 between about 40 µm and about 125 about 40 µm and about 115 µm, about 40 µm and about 100 µm, about 40 µm and about 90 µm, about 40 µm and about 80 µm, about 40 µm and about 70 µm, about 40 µm and about 60 µm, about 40 µm and about 50 µm, between about 50 µm and about 125 µm, about 50 µm and about 115 µm, about 50 µm and about 100 µm, about 50 µm and about 90 µm, about 50 µm and about 80 µm, about 50 µm and about 70 µm, about 50 µm and about 60 µm, between about 60 µm and about 125 µm, about 60 µm and about 115 µm, about 60 µm and about 100 µm, about 60 µm and about 90 µm, about 60 µm and about 80 µm, about 60 µm and about 70 µm, between about 70 µm and about 125 µm, about 70 µm and about 115 µm, about 70 µm and about 100 µm, about 70 µm and about 90 µm, about 70 µm and about 80 µm, between about 80 µm and about 125 µm, about 80 µm and about 115 µm, about 80 µm and about 100 µm, about 80 µm and about 90 µm, between about 90 µm and about 125 µm, about 90 µm and about 115 µm, about 90 µm and about 100 µm, between about 100 µm and about 125 µm, about 100 µm and about 115 µm, between about 115 µm and about 125 µm, about 20 µm, 30 µm, 40 µm, 50 µm, 60 µm, 70 µm, 80 µm, 90 µm, 100 µm, 115 µm, or about 120 µm. The nozzle is inert to both the solvent and the compressed fluid used in the methods.

In further examples, the system may include a plurality of nozzles, with each nozzle positioned at a different angle between a longitudinal axis of the vessel and a longitudinal axis of the nozzle and/or a different distance between the nozzle orifice and the sonic energy source. A given nozzle of the plurality of nozzles may be chosen for a given production run to produce a certain type of particle having a given SSA.

Any suitable solvent and solute may be used; exemplary such solutes and solvents are disclosed in U.S. Pat. Nos. 5,833,891 and 5,874,029. In one non-limiting embodiment, the solute/compound comprises a taxane, including those discussed herein. In various other non-limiting embodiments, the solvent may comprise acetone, ethanol, methanol, dichloromethane, ethyl acetate, chloroform, acetonitrile, and suitable combinations thereof. In one embodiment, the solute/compound is paclitaxel and the solvent is acetone. In another embodiment, the solute/compound is docetaxel and the solvent is ethanol. The solvents should comprise at least about 80%, 85%, or 90% by weight of the overall solution.

The compressed fluid is capable of forming a supercritical fluid under the conditions used, and the solute that forms the particles is poorly soluble or insoluble in the compressed fluid. As is known to those of skill in the art, a supercritical fluid is any substance at a temperature and pressure above its critical point, where distinct liquid and gas phases do not exist. Steps (a), (b), and (c) of the methods of the invention are carried out under supercritical temperature and pressure for the compressed fluid, such that the compressed fluid is present as a supercritical fluid during these processing steps.

The compressed fluid can serve as a solvent for and can be used to remove unwanted components in the particles. Any suitable compressed fluid may be used in the methods of the invention; exemplary such compressed fluids are disclosed in U.S. Pat. Nos. 5,833,891 and 5,874,029. In one non-limiting embodiment, suitable supercritical fluid-forming compressed fluids and/or anti-solvents can comprise carbon dioxide, ethane, propane, butane, isobutane, nitrous oxide, xenon, sulfur hexafluoride and trifluoromethane. The anti-solvent recited in step (d) to cause further solvent depletion, is a compressed fluid as defined above, and may be the same compressed fluid used in steps (a-c), or may be different. In one embodiment, the anti-solvent used in step (d) is the same as the compressed fluid used in steps (a-c). In a preferred embodiment, the compressed fluid and the anti-solvent are both super-critical carbon dioxide.

In all cases, the compressed fluid and anti-solvent should be substantially miscible with the solvent while the compound to be precipitated should be substantially insoluble in the compressed fluid, i.e., the compound, at the selected solvent/compressed fluid contacting conditions, should be no more than about 5% by weight soluble in the compressed fluid or anti-solvent, and preferably is essentially completely insoluble.

The supercritical conditions used in the methods of the invention are typically in the range of from 1× to about 1.4×, or 1× to about 1.2× of the critical temperature of the supercritical fluid, and from 1× to about 7×, or 1× to about 2×, of the of the supercritical pressure for the compressed fluid.

It is well within the level of those of skill in the art to determine the critical temperature and pressure for a given compressed fluid or anti-solvent. In one embodiment, the compressed fluid and anti-solvent are both super critical carbon dioxide, and the critical temperature is at least 31.1° C. and up to about 60° C., and the critical pressure is at least 1071 psi and up to about 1800 psi. In another embodiment, the compressed fluid and anti-solvent are both super critical carbon dioxide, and the critical temperature is at least 35° C. and up to about 55° C., and the critical pressure is at least 1070 psi and up to about 1500 psi. It will be understood by those of skill in the art that the specific critical temperature and pressure may be different at different steps during the processing.

Any suitable pressurizable chamber may be used, including but not limited to those disclosed in U.S. Pat. Nos. 5,833,891 and 5,874,029. Similarly, the steps of contacting the atomized droplets with the compressed fluid to cause depletion of the solvent from the droplets; and contacting the droplets with an anti-solvent to cause further depletion of the solvent from the droplets, to produce particles of the compound can be carried out under any suitable conditions, including but not limited to those disclosed in U.S. Pat. Nos. 5,833,891 and 5,874,029.

The flow rate can be adjusted as high as possible to optimize output but below the pressure limitations for the equipment, including the nozzle orifice. In one embodiment, the flow rate of the solution through the nozzle has a range from about 0.5 mL/min to about 30 mL/min. In various further embodiments, the flow rate is between about 0.5 mL/min to about 25 mL/min, 0.5 mL/min to about 20 mL/min, 0.5 mL/min to about 15 mL/min, 0.5 mL/min to about 10 mL/min, 0.5 mL/min to about 4 mL/min, about 1 mL/min to about 30 mL/min, about 1 mL/min to about 25 mL/min, about 1 mL/min to about 20 mL/min, 1 mL/min to about 15 mL/min, about 1 mL/min to about 10 mL/min, about 2 mL/min to about 30 mL/min, about 2 mL/min to about 25 mL/min, about 2 mL/min to about 20 mL/min, about 2 mL/min to about 15 mL/min, or about 2 mL/min to about 10 mL/min. The solution of drug subject to the flow rate can be any suitable concentration, such as between about 1 mg/ml and about 80 mg/ml.

In one embodiment, the methods further comprise receiving the plurality of particles through the outlet of the pressurizable chamber; and collecting the plurality of particles in a collection device.

In such an embodiment, with reference to the Figures, as shown in FIG. 5, the invention comprises a collection device 200 including a vessel 202 defining a chamber 204. The vessel 202 includes a distal end 206 and a proximal end 208. The outer diameter of the vessel 202 may range from about 152.4 mm to about 914.4 mm. The collection device 200 further includes an inlet port 210 extending from the proximal end 208 of the vessel 202. The inlet port 210 is in fluid communication with the chamber 204. The inlet port 210 may have an outer diameter ranging from about 12.7 mm to about 101.6 mm. Further, the collection device 200 includes an outlet port 212 extending from the proximal end 208 of the vessel 202. As shown in FIGS. 7 and 8, the outlet port 212 is in fluid communication with the chamber 204, and the outlet port 212 includes a porous material 214 positioned between the chamber 204 and the outlet port 212. The outer diameter of the outlet port may range from about 12.7 mm to about 50.8 mm.

As shown in FIGS. 5-9, the collection device 200 may further include a sampling tube 216 having a distal end 218 and a proximal end 220. The outer diameter of the sampling tube 216 may range from about 6.35 mm to about 25.4 mm. As shown in FIGS. 7 and 8, the proximal end 220 of the sampling tube 216 extends from the proximal end 208 of the vessel 202, and the distal end 218 of the sampling tube 216 extends into the chamber 204. The sampling tube 216 may be configured to remove a small sample of particles from the chamber 204 during a particle production run in which additional particles are being formed. In particular, the sampling tube 216 may include a sample thief that enables an operator to remove a small sample of particles without opening the chamber 204 or removing the sampling tube 216 from the rest of the collection device 200 during processing. This enables an operator to test a small sample of particles to ensure that the product is within specifications as the process continues to run. For example, particle size or residual solvent analysis may be performed on the sample. If the measured specifications do not match the desired specifications, the operating parameters of the particle formation process may be suitably adjusted to correct the situation before an entire batch of product with undesirable characteristics is created.

The porous material 214 positioned between the chamber 204 and the outlet port 212 may take a variety of forms. In one example, the porous material 214 is selected from the group consisting of a frit, a mesh, a cloth. As one specific example, the porous material 214 may comprise a high-efficiency particulate arrestance (HEPA) filter. An example HEPA filter may include a mat of randomly arranged fibers, the fibers composed of fiberglass and possessing diameters between about 0.5 micrometers and about 2.0 micrometers. In another example, the porous material 214 comprises a sintered filter having a distal end 222 and a proximal end 224. In such an example, the proximal end 224 of the sintered filter extends from the proximal end 208 of the vessel 202 and is coupled to the outlet port 212, and the distal end 222 of the sintered filter extends into the chamber 204. Such a sintered filter may include a porous stainless steel filter cartridge, as an example. Other porous materials are possible as well.

The inlet port 210 may include a coupling mechanism connects an outlet of a particle filtration system to the inlet port 210. In one example, the coupling mechanism comprises one or more sanitary fittings. In another example, the coupling mechanism comprises a threaded connection between the outlet of the particle filtration system to the inlet port 210. In yet another example, the coupling mechanism comprises one or more compression fittings. Other example coupling mechanisms are possible as well.

Figure 10:
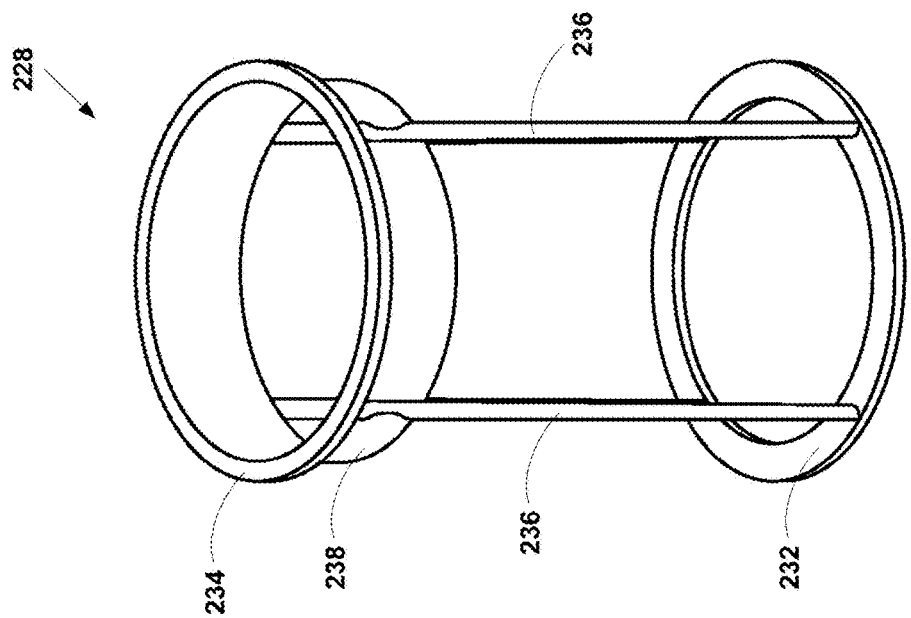
FIG. 10 illustrates a perspective view of a support frame, according to an example embodiment.
Figure 9:
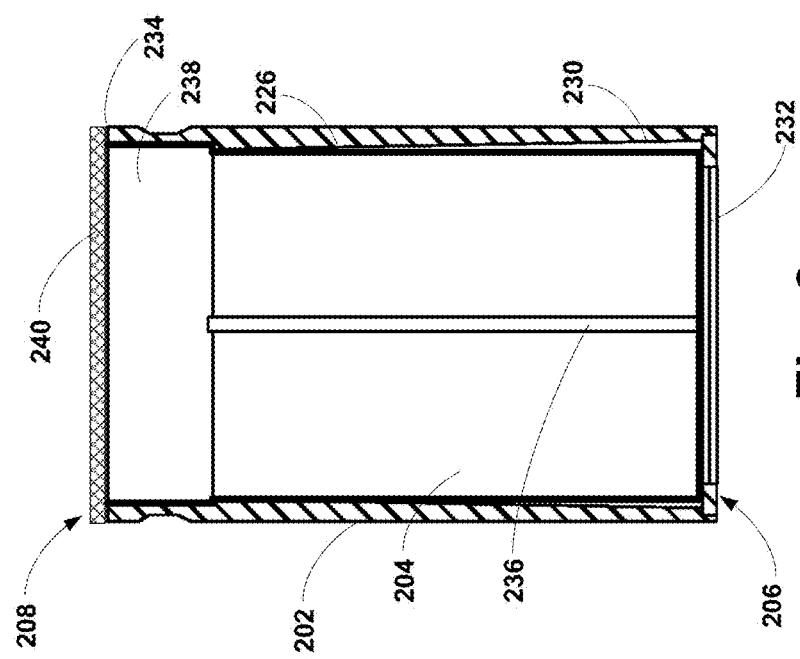
FIG. 9 illustrates another cross-section view of the particle collection device, according to an example embodiment.

Further, as shown in FIG. 9, the collection device 200 may further include a collection insert 226 positioned within the chamber 204 of the vessel 202, and a support frame 228 positioned between an interior wall 230 of the chamber 204 and the collection insert 226. The collection insert 226 may be a plastic bag, as an example. As shown in FIG. 10, the support frame 228 may include a distal ring 232, a proximal ring 234, one or more support legs 236 connecting the distal ring 232 to the proximal ring 234, and a gasket 238 positioned adjacent to the proximal ring 234. In one example, the gasket 238 may comprise a neoprene gasket. The vessel 202 may include a removable lid 240 that can be removed to access the collection insert 226 once particle collection is completed. In such an example, the collection insert 226 may be positioned within the chamber 204 of the vessel 202 such that top edge of the collection insert 226 folds over the top of the support frame 228 and is sealed between the gasket 238 and the removable lid 240 when the lid is in the closed position. Other arrangements are possible as well.

In one particular example method, a solution of 65 mg/ml of paclitaxel is prepared in acetone. The nozzle and a sonic probe are positioned in the pressurizable chamber approximately 8 mm apart. A stainless steel mesh filter with approximately 100 nm holes is attached to the pressurizable chamber to collect the precipitated paclitaxel nanoparticles. The supercritical carbon dioxide is placed in the pressurizable chamber of the manufacturing equipment and brought to approximately 1200 psi at about 37° C. and a flow rate of 18 kg per hour. The sonic probe is adjusted to an amplitude of 60% of maximum output at a frequency of 20 kHz. The acetone solution containing the paclitaxel is pumped through the nozzle at a flow rate of 2 mL/minute for approximately 60 minutes. The precipitated paclitaxel agglomerates and particles are then collected from the supercritical carbon dioxide as the mixture is pumped through the stainless steel mesh filter. The filter containing the nanoparticles of paclitaxel is opened and the resulting product is collected from the filter.

In one particular example method, a solution of 79.32 mg/ml of docetaxel is prepared in ethanol. The nozzle and a sonic probe are positioned in the pressurizable chamber approximately 9 mm apart. A stainless steel mesh filter with approximately 100 nm holes is attached to the pressurizable chamber to collect the precipitated docetaxel nanoparticles. The supercritical carbon dioxide is placed in the pressurizable chamber of the manufacturing equipment and brought to approximately 1200 psi at about 38° C. and a flow rate of 63 slpm (standard liters per minute). The sonic probe is adjusted to 60% of total output power at a frequency of 20 kHz. The ethanol solution containing the docetaxel is pumped through the nozzle at a flow rate of 2 mL/minute for approximately 95 minutes, until the drug solution is consumed. The precipitated docetaxel agglomerates and particles are then collected from the supercritical carbon dioxide as the mixture is pumped through the stainless steel mesh filter. The filter containing the nanoparticles of docetaxel is opened and the resulting product is collected from the filter.

Further, the system described above may be a component of a larger particle production system. Such a particle production system may include one or more nozzle assemblies such as those described above, a sonic energy source positioned adjacent to the orifice of each nozzle, one or more particle filtration systems in communication with one or more nozzle assemblies, and one or more particle collection devices in communication with the one or more particle filtration systems. In one example, the one or more particle filtration systems comprise a tandem particle filtration system including at least one high pressure harvesting filter system and at least one low pressure collection filter system in tandem and downstream to the harvesting filter. In such an example, the particle production system may include at least two particle harvesting filters, two particle collection filters and two collection devices.

In another aspect, the invention provides compound particles prepared by the method of any embodiment or combination of embodiments of the invention.

EXAMPLES

Materials and Methods

Raw paclitaxel and docetaxel were purchased from Phyton Biotech (British Columbia, Canada), lot number FP2-15004 and DT7-14025, respectively. Both were characterized in their raw form. The milling of both drugs was accomplished using a Deco-PBM-V-0.41 mill (Deco). The milling conditions for both compounds were as follows:
Ball size=5 mm
RPM=600
Processing time=60 min
Room temperature.

Preparation of Paclitaxel Particles

A solution of 65 mg/ml of paclitaxel was prepared in acetone. A BETE MicroWhirl® fog nozzle (BETE Fog Nozzle, Inc) and a sonic probe (Qsonica, model number Q700) were positioned in the crystallization chamber approximately 8 mm apart. A stainless steel mesh filter with approximately 100 nm holes was attached to the crystallization chamber to collect the precipitated paclitaxel nanoparticles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours. Paclitaxel nanoparticles produced had an average number-weighted mean size of 0.81 μm with an average standard deviation of 0.74 μm over three separate runs.

Preparation of Docetaxel Particles

A solution of 79.32 mg/ml of docetaxel was prepared in ethanol. The nozzle and a sonic probe were positioned in the pressurizable chamber approximately 9 mm (apart. A stainless steel mesh filter with approximately 100 nm holes was attached to the pressurizable chamber to collect the precipitated docetaxel nanoparticles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 95 minutes). The precipitated docetaxel agglomerates and particles were then collected from the supercritical carbon dioxide as the mixture is pumped through the stainless steel mesh filter. The filter containing the nanoparticles of docetaxel was opened and the resulting product was collected from the filter.

Docetaxel nanoparticles produced had an average number-weighted mean size of 0.82 μm with an average standard deviation of 0.66 μm over three separate ethanol runs.

Particle Size Analysis

Particle size was analyzed by both light obscuration and laser diffraction methods. An Particle Sizing Systems AccuSizer 780 SIS system was used for the light obscuration method and Shimadzu SALD-7101 was used for the laser diffraction method. Paclitaxel nanoparticles were analyzed using 0.10% (w/v) sodium dodecyl sulfate (SDS) in water as the dispersant. Docetaxel nanoparticles were analyzed using isopar G as the dispersant.

Paclitaxel suspensions were prepared by adding approximately 7 mL of filtered dispersant to a glass vial containing approximately 4 mg of paclitaxel particles. The vials were vortexed for approximately 10 seconds and then sonicated in a sonic bath approximately 1 minute. If the sample was already suspended, 1:1 solution of paclitaxel suspension to 0.1% SDS solution was made, vortexed for 10 seconds, and sonicated in the sonic bath for 1 minute.

Docetaxel suspensions were prepared by adding approximately 7 mL of filtered dispersant to a plastic vial containing approximately 4 mg of docetaxel particles. The vial was vortexed for approximately 10 seconds and then sonicated in a sonic bath for approximately 2 minutes. This suspension was used for laser diffraction analysis. Unused suspension was poured into a 125 mL particle-free plastic bottle, which was then filled to approximately 100 mL with filtered dispersant. The suspension was vortex for approximately 10 seconds and then sonicated in the sonic bath for approximately 2 minutes. This diluted suspension was used for light obscuration analysis.

A background test was first performed prior to analyzing particles on the AccuSizer 780 SIS. A new particle-free plastic bottle was filled with blank suspension solution by pumping from a reservoir, using a peristaltic pump, through a 0.22 µm Millipore filter and into the bottle. A background analysis was run to ensure the particle/mL count was below 100 particles/mL. A small amount of paclitaxel suspension, 5-100 µL depending upon concentration of solution, was pipetted into the plastic bottle in place from the background test and was filled with ~100 mL dispersant and the analysis was started. Counts were monitored and paclitaxel solution added to reach and/or maintain 6000-8000 particle counts/mL during the entire analysis. Once the analysis was completed, the background data was removed and any measurement with less than four counts was removed.

To analyze particles on SALD-7101 using a batch cell, the analysis was started by choosing Manual Measurement. The refractive index was set as 1.5 to 1.7. The batch cell was filled with filtered dispersant just past the etched line. The blank measurement was ran. A small amount of API (paclitaxel or docetaxel) suspension was pipetted, generally <1 mL, depending upon concentration of solution as low as 100 into the batch cell as needed to achieve an acceptable absorbance between 0.15 and 0.2 absorbance units. The measurements were executed, and the resulting graph with the highest level of confidence was selected; background was automatically accounted for.

BET Analysis

A known mass between 200 and 300 mg of the analyte was added to a 30 mL sample tube. The loaded tube was then mounted to a Porous Materials Inc. SORPTOMETER®, model BET-202A. The automated test was then carried out using the BETWIN® software package and the surface area of each sample was subsequently calculated.

Bulk Density Analyte

Paclitaxel or docetaxel particle preparations were added to a 10 mL tared graduated cylinder through a plastic weigh funnel at room temperature. The mass of the drug was measured to a nearest 0.1 mg, the volume was determined to the nearest 0.1 mL and the density calculated.

Dissolution Studies
Paclitaxel

Approximately 50 mg of material (i.e.: raw paclitaxel, milled paclitaxel, or paclitaxel particles) were coated on approximately 1.5 grams of 1 mm glass beads by tumbling the material and beads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 µm filter and analyzed on a U(V/V) is spectrophotometer at 227 nm. Absorbance values of the samples were compared to those of standard solutions prepared in dissolution media to determine the amount of material dissolved.

Docetaxel

Approximately 50 mg of material (i.e.: raw docetaxel, milled docetaxel, or docetaxel particles) was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 µm filter, and analyzed on a UV/VIS spectrophotometer at 232 nm. Absorbance values of the samples were compared to those of standard solutions prepared in dissolution media to determine the amount of material dissolved.

Results

The BET surface area of particles produced using the above protocol and variations thereof (i.e.: modifying nozzles, filters, sonic energy sources, flow rates, etc.) ranged between 22 and 39 $m^2/g$. FIG. 1 shows exemplary particles produced using the methods of the invention. By comparison, the BET surface area of raw paclitaxel was measured at 7.25 $m^2/g$ (FIG. 2), while paclitaxel particles made according to the methods of U.S. Pat. Nos. 5,833,891 and 5,874,029 ranged from 11.3 to 15.58 $m^2/g$. Exemplary particle sizes produced using the methods of the invention are shown in Table 1.

TABLE 1

| | Surface area | Mean Size μm | | St Dev μm | |
|---|---|---|---|---|---|
| | $m^2/g$ | Number | Volume | Number | Volume |
| 1 | 38.52 | 0.848 | 1.600 | 0.667 | 0.587 |
| 2 | 33.82 | 0.754 | 0.988 | 0.536 | 0.486 |
| 3 | 35.90 | 0.777 | 1.259 | 0.483 | 0.554 |
| 4 | 31.70 | 0.736 | 0.953 | 0.470 | 0.466 |
| 5 | 32.59 | 0.675 | 0.843 | 0.290 | 0.381 |
| 6 | 38.22 | 0.666 | 0.649 | 0.344 | 0.325 |
| 7 | 30.02 | 0.670 | 0.588 | 0.339 | 0.315 |
| 8 | 31.16 | 0.672 | 0.862 | 0.217 | 0.459 |
| 9 | 23.90 | 0.857 | 1.560 | 0.494 | 0.541 |
| 10 | 22.27 | 0.857 | 1.560 | 0.494 | 0.541 |
| 11 | 26.19 | 0.861 | 1.561 | 0.465 | 0.546 |

Comparative studies on bulk density, SSA, and dissolution rates (carried out as noted above) for raw drug, milled drug particles, and drug particles produced by the methods of the present invention are provided in Tables 2 and 3 below. The full dissolution time course for the paclitaxel and docetaxel materials are provided in Tables 4 and 5, respectively.

TABLE 2

| Compound: Paclitaxel | | | | | |
|---|---|---|---|---|---|
| | Raw | Particles | | | |
| Characteristic | Material | Batch 1 | Batch 2 | Mean | Milled |
| Number Mean (um) | 1.16 | 0.83 | 0.67 | 0.75 | 0.89 |
| Volume Mean (um) | 1.29 | 1.42 | 0.57 | 1.00 | 1.35 |
| Bulk Density ($g/cm^3$) | 0.26 | 0.060 | 0.11 | 0.085 | 0.31 |
| Surface Area ($m^2/g$) | 10.4 | 35.6 | 39.8 | 37.7 | 15.0 |
| Dissolution (30 min) | 18% | 42% | 52% | 47% | 32% |

TABLE 3

| Compound: Docetaxel | | | | | |
|---|---|---|---|---|---|
| | Raw | Particles | | | |
| Characteristic | Material | Batch 1 | Batch II | Mean | Milled |
| Number Mean (um) | 1.58 | 0.92 | 0.80 | 0.86 | 1.11 |
| Volume Mean (um) | 5.05 | 4.88 | 4.03 | 4.46 | 3.73 |
| Bulk Density ($g/cm^3$) | 0.24 | 0.062 | 0.096 | 0.079 | 0.44 |
| Surface Area ($m^2g$) | 15.9 | 43.0 | 45.4 | 44.2 | 15.2 |
| Dissolution (30 min) | 11% | 27% | 27% | 27% | 9% |

TABLE 4

| Paclitaxel Dissolution time course | | | |
|---|---|---|---|
| Timepoint (minutes) | Paclitaxel Raw Material | Paclitaxel Particles | Milled Paclitaxel |
| 0 | 0.0% | 0.0% | 0.0% |
| 10 | 14.0% | 40.2% | 23.0% |
| 20 | 17.8% | 47.6% | 30.0% |
| 30 | 18.4% | 51.9% | 32.3% |
| 60 | 23.9% | 58.3% | 38.6% |
| 90 | 28.6% | 62.9% | 43.5% |

TABLE 5

| Docetaxel Dissolution time course | | | |
|---|---|---|---|
| Timepoint (minutes) | Docetaxel Raw Material | Docetaxel Particles | Milled Docetaxel |
| 0 | 0.0% | 0.0% | 0.0% |
| 5 | 3.2% | 12.1% | 3.2% |
| 15 | 6.9% | 21.7% | 5.9% |
| 30 | 11.2% | 27.2% | 9.3% |
| 60 | 16.4% | 32.9% | 12.2% |
| 120 | 22.4% | 38.9% | 13.6% |
| 225 | 26.8% | 43.1% | 16.0% |

We claim:

1. A method for making paclitaxel or docetaxel particles, comprising:

(a) introducing (i) a solution comprising at least one solvent and at least one solute comprising paclitaxel or docetaxel into a nozzle inlet, and (ii) a compressed fluid into an inlet of a vessel defining a pressurizable chamber;

(b) passing the solution out of a nozzle orifice and into the pressurizable chamber to produce an output stream of atomized droplets, wherein the nozzle orifice is located between 4 mm and 20 mm from a sonic energy source located within the output stream, wherein the sonic energy source produces sonic energy with an amplitude between 10% and 60% during the passing, and wherein the nozzle orifice has a diameter of between 20 μm and 125 μm; and (c) contacting the atomized droplets with the compressed fluid, to cause depletion of the solvent from the atomized droplets, to produce paclitaxel or docetaxel particles, wherein steps (a), (b), and (c) are carried out under supercritical temperature and pressure for the compressed fluid.

2. The method of claim 1, further comprising:

(d) contacting the paclitaxel or docetaxel particles produced in step (c) with an anti-solvent to cause further depletion of the solvent from the paclitaxel or docetaxel particles, wherein step (d) is carried out under supercritical temperature and pressure for the anti-solvent.

3. The method of claim 1, wherein a flow rate of the solution through the nozzle has a range from about 0.5 mL/min to about 30 mL/min.

4. The method of claim 1, wherein the sonic energy source comprises one of a sonic horn, a sonic probe, or a sonic plate.

5. The method of claim 1, wherein the sonic energy source has a frequency of between about 18 kHz and about 22 kHz.

6. The method of claim 2, further comprising:

(e) receiving the plurality of paclitaxel or docetaxel particles through the outlet of the pressurizable chamber; and (f) collecting the plurality of particles in a collection device.

7. The method of claim 1, wherein the compressed fluid is super critical carbon dioxide.

8. The method of claim 2, wherein the anti-solvent is super critical carbon dioxide.

9. The method of claim 1, wherein the paclitaxel or docetaxel particles are paclitaxel particles and the solvent comprises acetone.

10. The method of claim 1, wherein the paclitaxel or docetaxel particles are docetaxel particles and the solvent comprises ethanol.

11. The method of claim 2, wherein the paclitaxel or docetaxel particles are paclitaxel particles and the solvent comprises acetone.

12. The method of claim 2, wherein the paclitaxel or docetaxel particles are docetaxel particles and the solvent comprises ethanol.

13. The method of claim 11, wherein the compressed fluid and the anti-solvent are super critical carbon dioxide.

14. The method of claim 12, wherein the compressed fluid and the anti-solvent are super critical carbon dioxide.

15. The method of claim 13, wherein the sonic energy source comprises one of a sonic horn, a sonic probe, or a sonic plate.

16. The method of claim 15, wherein the sonic energy source has a frequency of between about 18 kHz and about 22 kHz.

17. The method of claim 14, wherein the sonic energy source comprises one of a sonic horn, a sonic probe, or a sonic plate.

18. The method of claim 17, wherein the sonic energy source has a frequency of between about 18 kHz and about 22 kHz.

* * * * *